(12) United States Patent  
Dorrough

(10) Patent No.: US 8,736,283 B2
(45) Date of Patent: *May 27, 2014

(54) ADVANCED OBSCURED FEATURE DETECTOR

(75) Inventor: David M. Dorrough, Eagle, ID (US)

(73) Assignee: Franklin Sensors Inc., Eagle, ID (US)

( * ) Notice: Subject to any disclaimer, the term of this patent is extended or adjusted under 35 U.S.C. 154(b) by 490 days.

This patent is subject to a terminal disclaimer.

(21) Appl. No.: 13/040,203

(22) Filed: Mar. 3, 2011

(65) Prior Publication Data

US 2011/0215814 A1    Sep. 8, 2011

Related U.S. Application Data

(60) Provisional application No. 61/339,316, filed on Mar. 4, 2010, provisional application No. 61/333,252, filed on May 10, 2010, provisional application No. 61/345,591, filed on May 17, 2010, provisional application No. 61/433,954, filed on Jan. 18, 2011, provisional application No. 61/436,188, filed on Jan. 25, 2011, provisional application No. 12/860,448, filed on Aug. 20, 2010.

(51) Int. Cl.
*G01R 27/26*    (2006.01)
*G01R 19/00*    (2006.01)

(52) U.S. Cl.
USPC ............................................ 324/663; 324/67

(58) Field of Classification Search
USPC ............. 324/663, 658, 649, 600, 326, 66, 67; 33/354, 332, 286, 666
See application file for complete search history.

(56) References Cited

U.S. PATENT DOCUMENTS

| | | | |
|---|---|---|---|
| 4,099,118 A | 7/1978 | Franklin et al. | |
| 4,464,622 A | 8/1984 | Franklin | |
| 4,853,617 A * | 8/1989 | Douglas et al. | 324/67 |
| 4,992,741 A | 2/1991 | Douglas et al. | |
| 5,214,388 A | 5/1993 | Vranish et al. | |
| 5,325,442 A | 6/1994 | Knapp | |
| 5,352,974 A | 10/1994 | Heger | |
| 5,619,128 A | 4/1997 | Heger | |
| 5,682,032 A | 10/1997 | Philipp | |
| 5,730,165 A | 3/1998 | Philipp | |
| 5,773,971 A | 6/1998 | Tavernetti | |

(Continued)

FOREIGN PATENT DOCUMENTS

EP    1622266 A1    2/2006

OTHER PUBLICATIONS

International Search Report and Written Opinion dated Sep. 15, 2011 for PCT/US2011/027239.

(Continued)

*Primary Examiner* — Hoai-An D Nguyen
(74) *Attorney, Agent, or Firm* — Parsons Behle & Latimer

(57) ABSTRACT

A surface-conforming obscured feature detector includes a plurality of sensor plates, each having a capacitance that varies based on the dielectric constant of the materials that compose the surrounding objects and the proximity of those objects. A sensing circuit is coupled to the sensor plates 32 to measure the capacitances of the sensor plates. A controller is coupled to the sensing circuit to analyze the capacitances measured by the sensing circuit. One or a plurality of indicators are coupled to the controller, and are selectively activated to identify the location of an obscured feature behind a surface.

9 Claims, 16 Drawing Sheets

(56) References Cited

U.S. PATENT DOCUMENTS

| | | |
|---|---|---|
| 5,844,486 A | 12/1998 | Kithil et al. |
| 5,917,314 A | 6/1999 | Heger et al. |
| 6,023,159 A | 2/2000 | Heger |
| 6,152,514 A | 11/2000 | McLellen |
| 6,198,271 B1 | 3/2001 | Heger et al. |
| 6,211,662 B1 | 4/2001 | Bijawat et al. |
| 6,215,293 B1 | 4/2001 | Yim |
| 6,249,113 B1 | 6/2001 | Krantz et al. |
| 6,259,241 B1 | 7/2001 | Krantz |
| 6,288,707 B1 | 9/2001 | Philipp |
| 6,370,965 B1 | 4/2002 | Knapp |
| 6,377,009 B1 | 4/2002 | Philipp |
| 6,446,012 B1 | 9/2002 | Macke, Sr. et al. |
| 6,452,514 B1 | 9/2002 | Philipp |
| 6,457,355 B1 | 10/2002 | Philipp |
| 6,466,036 B1 | 10/2002 | Philipp |
| 6,501,414 B2 | 12/2002 | Arndt et al. |
| 6,535,200 B2 | 3/2003 | Philipp |
| 6,844,713 B2 | 1/2005 | Steber et al. |
| 6,894,505 B2 | 5/2005 | Gohel |
| 6,989,662 B2 | 1/2006 | Heger et al. |
| 6,993,607 B2 | 1/2006 | Philipp |
| 7,013,570 B2 | 3/2006 | Levine et al. |
| 7,106,072 B2 | 9/2006 | Clauss et al. |
| 7,116,091 B2 | 10/2006 | Miller |
| 7,148,703 B2 | 12/2006 | Miller |
| 7,212,014 B2 | 5/2007 | Krantz |
| 7,256,587 B2 | 8/2007 | Sanoner et al. |
| 7,288,945 B2 | 10/2007 | Martinez et al. |
| 7,316,073 B2 | 1/2008 | Murray |
| 7,409,765 B2 | 8/2008 | So |
| 2005/0138886 A1 | 6/2005 | Sanoner |
| 2005/0194959 A1 | 9/2005 | Miller |
| 2008/0238403 A1 | 10/2008 | Sanoner |
| 2009/0045808 A1* | 2/2009 | Mano ............................ 324/220 |
| 2011/0215815 A1* | 9/2011 | Dorrough ..................... 324/663 |
| 2011/0215816 A1* | 9/2011 | Dorrough ..................... 324/663 |
| 2011/0215817 A1* | 9/2011 | Dorrough ..................... 324/663 |
| 2011/0215818 A1* | 9/2011 | Dorrough ..................... 324/679 |
| 2011/0215819 A1* | 9/2011 | Dorrough ..................... 324/684 |
| 2011/0215822 A1* | 9/2011 | Dorrough ..................... 324/687 |

OTHER PUBLICATIONS

US Patent and Trademark Office; Non-Final Office Action for U.S. Appl. No. 12/860,448 dated Aug. 15, 2012.

US Patent and Trademark Offcie, Office Action Dated Sep. 17, 2012 for U.S. Appl. No. 12/826,478.

* cited by examiner

Predetermined Pattern A – Values of the pattern shown in FIG. 11
    10  50  62  72  80  100  80  72  62  50  10  7  3

Predetermined Pattern B – Values of the pattern shown in FIG. 12
    18  48  61  79  100  100  79  61  48  18  6  3  0

Measured Reading Pattern
    12  54  61  74  83  98  81  70  59  44  7  5  2

Error Values with Pattern A: Absolute value of the difference between the values of Predetermined Pattern A and the values of the Measured Reading Pattern
    2  4  1  2  3  2  1  2  3  6  3  2  1
                        Score (Sum of Error Values): 32

Error Values with Pattern B: Absolute value of the difference between the values of Predetermined Pattern B and the values of the Measured Reading Pattern
    6  6  0  5  17  2  2  9  11  22  1  2  2
                        Score (Sum of Error Values): 85

Table 1

FIG. 14

Predetermined Pattern A — Values of the pattern shown in FIG. 11
    10  50  62  72  80  100  80  72  62  50  10  6  3

Pattern A Slopes -- Slopes between values of Predetermined Pattern A
    40  12  10  8  20  -20  -8  -10  -12  -40  -4  -3

Predetermined Pattern B — Values of the pattern shown in FIG. 12
    18  48  61  79  100  100  79  61  48  18  6  3  0

Pattern B Slopes -- Slopes between values of Predetermined Pattern B
    30  13  18  21  0  -21  -18  -13  -30  -12  -3  -3

Measured Reading Pattern
    12  54  61  74  83  98  81  70  59  44  7  5  2

Measured Reading Pattern Slopes -- Slopes between values of the Measured Reading Pattern
    32  7  13  9  15  -17  -11  -11  -15  -37  -2  -3

Error Values with Pattern A: Absolute value of the difference between Pattern A Slopes and Measured Reading Pattern Slopes
    8  5  3  1  5  3  3  1  3  3  2  0
                    Score (Sum of Error Values): 32

Error Values with Pattern B: Absolute value of the difference between Pattern B Slopes and Measured Reading Pattern Slopes
    2  6  5  12  15  4  7  2  15  25  1  0
                    Score (Sum of Error Values): 94

Table 2

FIG. 15

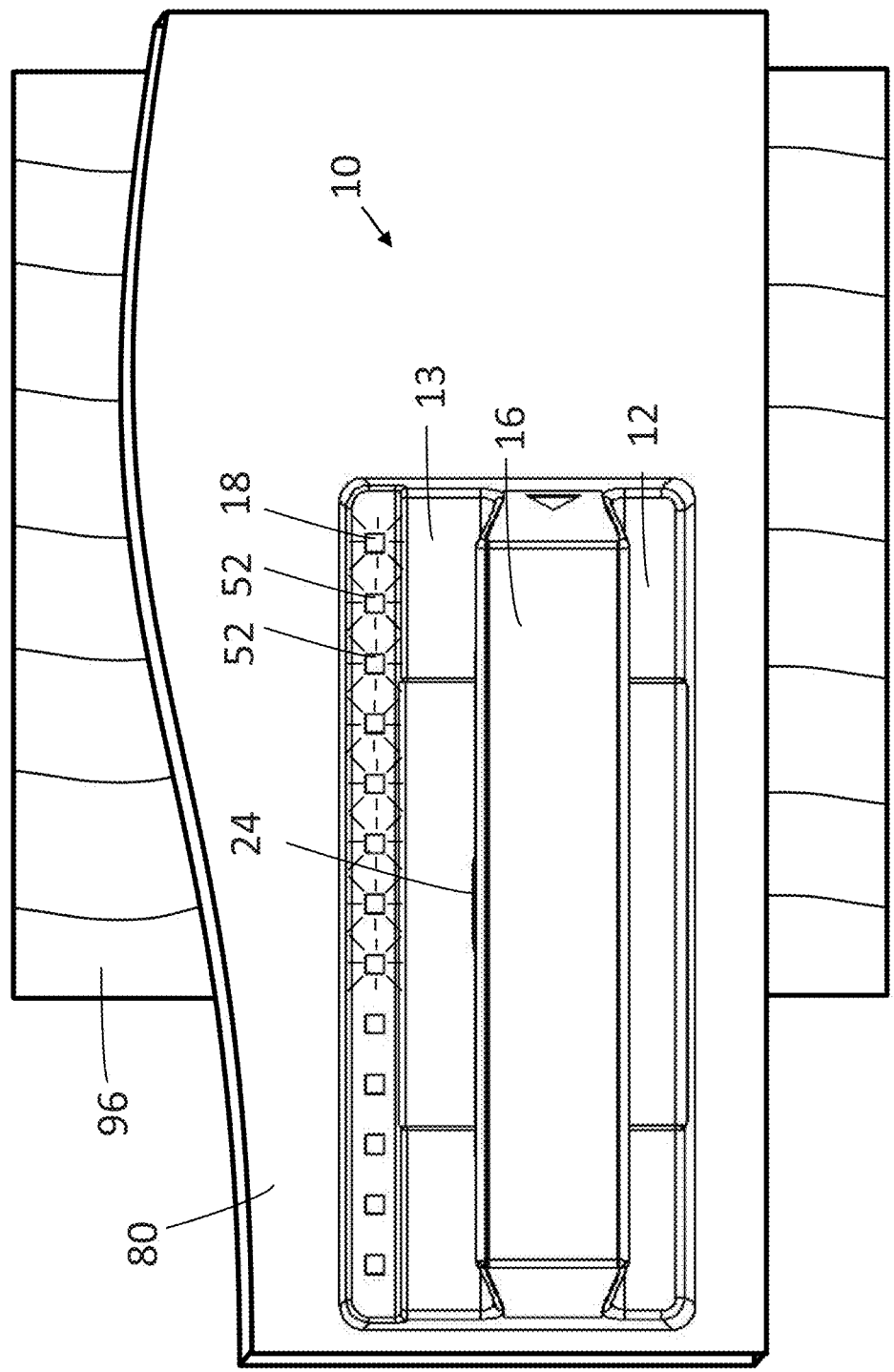

ADVANCED OBSCURED FEATURE DETECTOR

CROSS REFERENCE TO RELATED APPLICATIONS

This application claims benefit of the following patent applications: U.S. Provisional Patent Application No. 61/339,316, entitled "MATERIAL DETECTOR THAT OPERATES FROM A STATIONARY POSITION" and filed on Mar. 4, 2010; U.S. Provisional Patent Application No. 61/333,252, entitled "MATERIAL DETECTOR THAT OPERATES FROM A STATIONARY POSITION" and filed on May 10, 2010; U.S. Provisional Patent Application No. 61/345,591, entitled "MATERIAL DETECTOR THAT OPERATES FROM A STATIONARY POSITION" and filed on May 17, 2010; U.S. Provisional Patent Application No. 61/433,954, entitled "OBSCURED FEATURE DETECTOR" and filed on Jan. 18, 2011; U.S. Provisional Patent Application No. 61/436,188, entitled "OBSCURED FEATURE DETECTOR" and filed on Jan. 25, 2011; U.S. Non-Provisional patent application Ser. No. 12/826,478 entitled "STATIONARY FEATURE DETECTOR" and filed on Jun. 29, 2010; U.S. Non-Provisional patent application Ser. No. 12/860,448 entitled "SURFACE-CONFORMING OBSCURED FEATURE DETECTOR" and filed on Aug. 20, 2010. The entire contents of these patent applications are incorporated by reference herein.

BACKGROUND

1. Technical Field

The present disclosure relates generally to devices used for detecting the presence of obscured features behind opaque, solid surfaces, more specifically, devices used for locating beams and studs behind walls and joists beneath floors.

2. Background

The need to locate obscured features such as beams, studs, joists and other support elements behind walls and beneath floors is a common problem encountered during construction, repair and home improvement activities. Often a need exists to cut or drill into a supported surface with the aim of creating an opening in the surface while avoiding the underlying support elements. In these instances, it is desirable to know where the support elements are positioned before beginning so as to avoid cutting or drilling into them. On other occasions, one may desire to anchor a heavy object to the obscured support element. In these cases, it is often desirable to install a fastener through the surface in alignment with the underlying support element. However, once the wall, floor or surface is in place, the location of the support element is not visually detectable A variety of rudimentary techniques have been employed with limited success to address this problem in the past. These have included driving small pilot nails through the surface until a support element is detected and then covering over holes in the surface that did not reveal the location of the stud or support. A less destructive technique comprises tapping on the surface in question with the aim of detecting audible changes in the sound which emanates from the surface when there is a support element beneath or behind the area being tapped. This technique is not very effective, however, because the accuracy of the results depends greatly on the judgment and skill of the person searching for the support, and because the sound emitted by the tapping is heavily influenced by the type and density of the surface being examined.

Magnetic detectors have also been employed to find obscured support elements with the detector relying on the presence of metallic fasteners, such as nails or screws, in the wall and support element to trigger a response in the detector. However, since metallic fasteners are spaced at discrete locations along the length of a support, a magnetic detector may pass over a length of the support where no fasteners are located, thereby failing to detect the presence of the obscured support element.

Capacitive sensors have also been employed to detect obscured features behind opaque surfaces. These detectors sense changes in capacitance on the examined surface that result from the presence of features positioned behind, beneath or within the surface. These changes in capacitance are detectable through a variety of surfaces such as wood, sheet-rock, plaster, gypsum and do not rely on the presence of metal fasteners in the surface or obscured feature for activation of the sensor.

However, conventional capacitive sensors often suffer from a number of shortcomings. For example, conventional capacitive sensors typically require movement across an examined surface, sometimes repeatedly, to effectively locate an obscured feature or support element. In addition, capacitive sensors generally can only locate one feature at a time, and often can only find the edge of the feature rather than its center point. Some capacitive sensors rely on an assumed width of a feature to calculate the location of the center of the feature based on detection of the edge. Such devices frequently require a comparison circuit in addition to a sensing circuit in order to compare capacitances sensed by different sensors.

SUMMARY

The present disclosure advantageously addresses one or more of the aforementioned deficiencies in the field of obscured feature detection by providing an accurate, simple to use and inexpensively manufactured obscured feature detector. The detector can be employed by placing the device against the examined surface and reading the location of all features present beneath the surface where the device is positioned.

In one embodiment, an obscured feature detector comprises a plurality of sensor plates, each having a capacitance that varies based on: (a) the proximity of the sensor plate to one or more surrounding objects, and (b) the dielectric constant(s) of the surrounding object(s). The obscured feature detector further comprises a sensing circuit coupled to the sensor plates, the circuit being configured to measure the capacitances of the sensor plates, the set of measured capacitance values comprising a measured reading pattern. The obscured feature detector further comprises a pattern matching module configured to compare the measured reading pattern with a plurality of predetermined patterns and determine which predetermined pattern best matches the measured reading pattern, and one or a plurality of indicators coupled to the controller, each indicator capable of toggling between a deactivated state and an activated state. The controller is configured to activate one or more of the indicators to identify a location of an obscured feature.

At least one of the predetermined patterns may have values that are consistent with the detector performing a reading on sheetrock with a single stud behind the sheetrock. At least one of the predetermined patterns may have values that are consistent with the detector performing a reading on sheetrock with two studs behind the sheetrock, the two studs separated by a distance of at least about two inches. The obscured feature detector may comprise at least four sensor plates. The indicators may be LEDs. The pattern matching module may be configured to compare the values of the measured reading pattern to the values of a predetermined pattern. The pattern matching module may be configured to compare the slopes of the measured reading pattern to the slopes of a predetermined pattern, wherein the slopes of the measured reading pattern may be calculated by comparing neighboring measured capacitance values and the slopes of the predetermined pattern may be calculated by comparing neighboring values. The plurality of predetermined patterns may comprise at least 30 unique patterns. Each of the sensor plates may be substantially the same size. The plurality of predetermined patterns may include multiple patterns corresponding to a single stud, where each of the multiple patterns may correspond to a single stud in a different location. The obscured feature detector may comprise a non-volatile memory that stores the plurality of sensor read patterns. The pattern matching module may be configured to calculate the plurality of sensor read patterns and store them in memory when the obscured feature detector is initialized. The pattern matching module may be configured to calculate the plurality of sensor read patterns and store them in memory when a calibration routine in executed. Finally, the pattern matching module may be configured to calculate the plurality of sensor read patterns in real-time, when the obscured feature detector is in use.

In one embodiment, a method for determining the location of obscured features behind a surface comprises placing an obscured feature detector on the surface, the obscured feature detector having a plurality of sensor plates arranged in an array, measuring capacitance readings sensed in a plurality of regions, each region corresponding to an area surrounding one or more of the sensor plates, the set of capacitance readings forming a measured reading pattern. The method includes the step of comparing the measured reading pattern to each of a plurality of predetermined patterns, each predetermined pattern comprising a set of values, identifying, based upon comparisons of the measured reading pattern to the predetermined patterns, the predetermined pattern that best matches the measured reading pattern, and each predetermined pattern being associated with one or more indicators. The method also comprises the step of activating the one or more indicators associated with the predetermined pattern that best matches the measured reading pattern.

At least one of the predetermined patterns may have values that are consistent with the detector performing a reading on sheetrock with a single stud behind the sheetrock. At least one of the predetermined patterns may have values that are consistent with the detector performing a reading on sheetrock with two studs behind the sheetrock, the two studs being located adjacent to each other. At least one of the predetermined patterns may have values that are consistent with the detector performing a reading on sheetrock with two studs behind the sheetrock, the two studs being separated by a distance of at least about two inches. At least one predetermined pattern may be associated with one or more indicators spanning a distance of at least about one and one half inches. And at least one predetermined pattern may be associated with one or more indicators that indicate the edges of an obscured feature.

In one embodiment, an obscured feature detector comprises a plurality of sensor plates, each having a capacitance that varies based on: (a) the proximity of the sensor plate to one or more surrounding objects, and (b) the dielectric constant(s) of the surrounding object(s). The obscured feature detector further comprises a sensing circuit coupled to the sensor plates, the circuit being configured to measure the capacitances of the sensor plates, a controller coupled to the sensing circuit, the controller being configured to analyze the capacitances measured by the sensing circuit, and one or more indicators coupled to the controller, each indicator capable of toggling between a deactivated state and an activated state. When the controller detects two or more obscured features, the controller is configured to activate two or more indicators simultaneously to identify the locations of the two or more obscured features.

The detector may be at least approximately seven inches wide. The number of sensor plates may be 4 or greater. Each of the sensor plates may be substantially the same size. The detector may be capable of detecting three or more features simultaneously. The detector may be capable identifying the width of more than one feature. The obscured feature detector may further comprise a pattern matching module that may be configured to compare the measured capacitance readings with a plurality of predetermined patterns and determine which predetermined pattern best matches the measured capacitance readings.

In another embodiment, a method for determining the location of a plurality of obscured features behind a surface comprises placing an obscured feature detector on the surface, the obscured feature detector having a plurality of sensor plates arranged in an array, measuring capacitance readings sensed in a plurality of regions, each region corresponding to an area surrounding one or more of the sensor plates, identifying, based upon the measured capacitance readings, the location of the plurality of obscured features, and activating a plurality of indicators simultaneously to identify the locations of the plurality of obscured features.

Identifying the location of the plurality of obscured features may comprise using a pattern matching module to determine the locations of the plurality of obscured features.

In one embodiment, an obscured feature detector comprises a plurality of sensor plates, each having a capacitance that varies based on: (a) the proximity of the sensor plate to one or more surrounding objects, and (b) the dielectric constant(s) of the surrounding object(s). The obscured feature detector further comprises a sensing circuit coupled to the sensor plates, the circuit being configured to measure the capacitances of the sensor plates, a controller coupled to the sensing circuit, the controller being configured to analyze the capacitances measured by the sensing circuit, and one or more indicators coupled to the controller, each indicator capable of toggling between a deactivated state and an activated state. The controller is configured to activate one or more of the indicators to identify both a location and a width of an obscured feature.

The detector may use a pattern matching module to determine the width of obscured features. The detector may activate indicators that are in front of an obscured feature to indicate the width of the obscured features. A larger number of activated indicators may indicate that an obscured feature is wider, and a smaller number of activated indicators may indicate that an obscured feature is narrower.

In another embodiment, an obscured feature detector comprises a plurality of sensor plates, each having a capacitance that varies based on: (a) the proximity of the sensor plate to one or more surrounding objects, and (b) the dielectric constant(s) of the surrounding object(s). The obscured feature detector further comprises a sensing circuit coupled to the sensor plates, the circuit being configured to measure the capacitances of the sensor plates, a controller coupled to the sensing circuit, the controller being configured to analyze the capacitances measured by the sensing circuit, and one or a plurality of indicators coupled to the controller, each indicator capable of toggling between a deactivated state and an activated state. The controller is configured to activate one or more of the indicators to identify a location of an obscured feature such that indicators that are in front of an obscured feature are activated.

In another embodiment, a method for determining the location of more than one obscured features behind a surface comprises placing an obscured feature detector on the surface, the obscured feature detector having a plurality of sensor plates arranged in an array, measuring capacitance readings sensed in a plurality of regions, each region corresponding to an area surrounding one or more of the sensor plates, identifying, based upon the measured capacitance readings, the location of an obscured feature, and activating the indicator(s) in front of the obscured feature to identify both the location and the width of the obscured feature.

In one embodiment, an obscured feature detector comprises a plurality of sensor plates, each having a capacitance that varies based on: (a) the proximity of the sensor plate to one or more surrounding objects, and (b) the dielectric constant(s) of the surrounding object(s). The obscured feature detector further comprises a sensing circuit coupled to the sensor plates, the circuit being configured to measure the capacitances of the sensor plates, a controller coupled to the sensing circuit, the controller being configured to analyze the capacitances measured by the sensing circuit, and one or more indicators coupled to the controller, each indicator capable of toggling between a deactivated state and an activated state. The controller is configured to activate one or more of the indicators to identify both a location and a width of an obscured feature, and the controller is configured to detect electromagnetic fields.

The sensing circuit may be configured to perform capacitive readings at a frequency that is higher than the electromagnetic field frequency detected by the sensor plates. The sensing circuit may be configured to perform capacitive readings at a frequency that is an inharmonic of the electromagnetic field frequency detected by the sensor plates. The sensing circuit may be configured to perform capacitive reads at least 150 times per second. The controller may be configured to compare multiple capacitive readings associated with a given region to calculate the amount of disparity in the readings. The obscured object detector may be configured such that regions with greater disparity of readings as compared to the detector's other regions, are identified as regions that are closer to an alternating electromagnetic field. The detector may further comprise a disparity reading pattern that may be defined by the a plurality of the disparity readings, and a pattern matching module that may be configured to compare the disparity reading pattern with a plurality of predetermined patterns to determine which predetermined pattern best matches the disparity reading pattern. The controller may be optimized to detect electromagnetic fields with a frequency of approximately 50 to 60 Hz. The obscured feature detector may comprise at least four sensor plates.

In one embodiment, a method for determining the location of an alternating electromagnetic field comprises placing an electromagnetic field detector on a surface, the electromagnetic field detector having a plurality of sensor plates arranged in an array, taking capacitance readings in an area surrounding one or more of the sensor plates, identifying, based upon the capacitance readings, the location of one or a plurality of alternating electromagnetic fields, and activating one or a plurality of indicators to promote visual identification of the location of an alternating electromagnetic field.

Capacitive readings may be taken at a higher frequency than the frequency of the detected electromagnetic field(s). Capacitive readings may be taken at a frequency that is an inharmonic of the frequency of the detected electromagnetic field(s). Capacitive readings may be taken at least 150 times per second. Multiple capacitive readings from a single area may be compared to each other to determine disparity factors representing the amount of disparity in the capacitive readings. Areas with more disparity in the readings may be identified as areas that are closer to an alternating electromagnetic field. Values that represent the disparity in the capacitance readings may define a disparity reading pattern, and the disparity reading pattern may be compared to a plurality of predetermined patterns to identify the predetermined pattern that best matches the disparity reading pattern. And the array of sensor plates may comprise at least four sensor plates.

In another embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the sensor plates by a plurality of electrically conductive paths, the sensing circuit being configured to measure the capacitances of the sensor plates, the electrically conductive paths having a length defined by the distance along the paths between the sensor plates and the sensing circuit, and two or more of the electrically conductive path lengths are substantially the same.

Two or more of the electrically conductive paths may have a width which is substantially the same. The electrically conductive paths may comprise a first segment and a second segment, wherein the first segment may have a constant first width, and the second segment may have a constant second width. Each of the sensor plates may have a length defined by the distance from a first surface to an opposite second surface of a plate, and each sensor plate may have substantially the same length. Each of the sensor plates may have a width defined by the distance from a third surface to an opposite fourth surface of a plate, and each sensor plate may have substantially the same width. Each of the sensor plates may have a thickness defined by the distance from a top surface to a bottom surface of a plate, and each sensor plate may have substantially the same thickness. A portion of the electrically conductive path may comprise a copper trace on a printed circuit board. The obscured feature detector may further comprise a controller coupled to the sensing circuit, the controller being configured to analyze the capacitance in the area surrounding each sensor plate measured by the sensing circuit, and one or a plurality of indicators may be coupled to the controller, each indicator capable of toggling between a deactivated state and an activated state. The controller may be configured to activate one or more of the indicators to identify a location of an obscured feature.

In another embodiment, a method of using an obscured feature detector having a plurality of sensor plates to determine the location of an obscured feature behind a surface comprises placing the obscured feature detector on the surface, transmitting a value from the plurality of sensor plates along a plurality electrically conductive paths to a sensor circuit, wherein the length of at least two of the conductive paths is substantially equal, measuring capacitance readings sensed in a plurality of regions, each region corresponding to an area surrounding one or more of the sensor plates and represented by the value transmitted from the plurality of sensor plates, and identifying, based on the capacitance readings, a location of the obscured feature behind the surface.

The method may further comprise activating one or more indicators to indicate the location of the obscured feature behind the surface. The sensor plates may each have a length that is substantially the same. The sensor plates may each have a width that is substantially the same. The sensor plates may each have a thickness that is substantially the same. A portion of the electrically conductive path may comprise a copper trace on a printed circuit board. A first segment of an electrically conductive path may be located on a first layer of a printed circuit board, and a second segment of an electrically conductive path may be located on a second layer of a printed circuit board. Two or more of the electrically conductive paths may have substantially the same width. And the electrically conductive paths may have a first segment and a second segment; the first segment may have a substantially constant first width, and the second segment may have a substantially constant second width.

In one embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the sensor plates via a plurality of sensor plate traces, the sensing circuit being configured to measure the capacitance of each of the sensor plates, and a plurality of shield traces located adjacent to the sensor plate traces and configured to provide a substantially uniform electrical environment for two or more of the sensor plate traces.

The obscure feature detector may further comprise a controller coupled to the sensing circuit, the controller may be configured to analyze the capacitances measured by the sensing circuit, one or a plurality of indicators may be coupled to the controller, and each indicator may be capable of toggling between a deactivated state and an activated state. The controller may be configured to activate one or more of the indicators to identify a location of an obscured feature. The shield traces may be substantially parallel to the sensor plate traces. The shield traces may be positioned such that the shield traces shield the sensor plate traces from external electromagnetic fields. Each sensor plate trace may have one or more respective shield traces. The sensor plate traces and shield traces may be positioned such that capacitance between each sensor plate trace and each shield trace is substantially the same for each sensor plate trace and its respective shield trace. A sensor plate trace may be accompanied by two shield traces, such that one shield trace is positioned on each side of the sensor plate trace. A sensor plate trace and a shield trace may be positioned such that there is a constant distance between a sensor plate trace and the respective shield trace, along their length. Each of the shield traces may be positioned at a uniform distance away from the respective sensor plate trace. A segment of the each sensor plate trace and a segment of each shield trace may comprise copper traces on a printed circuit board. The sensor plate traces and shield traces may both be located on the same layer of a printed circuit board. The shield traces may be driven at a fixed voltage level. And the shield traces may be driven at a voltage that is similar to the voltage driven on the sensor plate traces.

In one embodiment, an obscured feature detector comprises an array of a plurality of sensor plates, each having a capacitance that varies based on: (a) the proximity of the sensor plates to one or more surrounding objects, and (b) the dielectric constant(s) of the surrounding object(s). The obscured feature detector may further comprise a sensing circuit coupled to the sensor plates, the sensing circuit being configured to measure the capacitance of each of the sensor plates, and a controller coupled to the sensing circuit, the controller being configured to analyze the capacitances measured by the sensing circuit. The array of sensor plates and the sensing circuit is supported by a housing that includes a gripping surface, the array of sensor plates are arranged in series, and the gripping surface is largely parallel to the array of sensor plates such that the array of sensor plates and the gripping surface are largely parallel. The obscured feature detector further comprises one or a plurality of indicators coupled to the controller, each indicator capable of toggling between a deactivated state and an activated state, and the controller is configured to activate one or more of the indicators to identify a location of an obscured feature.

The gripping surface may be oriented such that when the detector is held on a wall in a position to detect vertical studs, four or more fingers are lined up with an orientation that is more horizontal than vertical. The housing may comprise plastic, and the gripping surface may comprise an elastomer. The gripping surface may be a curved surface, and it may also be a flat surface.

In one embodiment, a method for using an obscured object detector with a plurality of sensor plates to detect an object behind an obscuring surface comprises orienting the obscured object detector on the obscuring surface such that the plurality of sensor plates define an array that is substantially horizontal, and gripping the obscured object detector on a predefined gripping region defined on an exterior surface of the obscured object detector, wherein the gripping regions are substantially parallel to the sensor plate array.

In another embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The detector has a housing comprising a bottom portion that houses the plurality of sensor plates. A layer of material is attached to the bottom portion of the detector, wherein the material comprises plastic.

The obscured feature detector may further comprise a sensing circuit coupled to the sensor plates, the sensing circuit being configured to measure the capacitances of the sensor plates, a controller coupled to the sensing circuit, the controller being configured to analyze the capacitances measured by the sensing circuit, and/or one or a plurality of indicators coupled to the controller, each indicator capable of toggling between a deactivated state and an activated state. The controller may be configured to activate one or more of the indicators to identify a location of an obscured feature. And the layer of material may comprise ultra-high molecular weight polyethylene.

In one embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the plurality of sensor plates, the sensing circuit being configured to measure the capacitance of each of the sensor plates, and a controller coupled to the sensing circuit, the controller being configured to receive the capacitance measurements from the sensing circuit. The controller is configured to operate in a first mode and a second mode, the first mode configured to detect obscured features of a predetermined first material, and the second mode configured to detect obscured features of a predetermined second material. One or a plurality of indicators are coupled to the controller, each indicator capable of toggling between a deactivated state and an activated state, and the controller is configured to activate one or more of the indicators to identify a location of an obscured feature.

The first predetermined material may be wood. The second predetermined material may be metal or plastic. A measured reading pattern may be defined by a set of measured capacitance values, the first mode configured to use a pattern matching module, the pattern matching module being configured to compare the measured reading pattern with a plurality of predetermined patterns to identify the predetermined pattern that best matches the measured reading pattern. One or more of the predetermined patterns may have capacitance values representing obscured features that comprise wood. The second mode may be configured to use a pattern matching module, the pattern matching module being configured to compare the measured reading pattern with a plurality of predetermined patterns to identify the predetermined pattern that best matches the measured reading pattern, and one or more of the predetermined patterns may have capacitance values representing obscured features that comprise metal. The first mode, or second mode, can be selected via an actuator. The controller may select the mode of operation, or the controller may automatically select the mode. The controller may also automatically select the mode after the capacitances have been measured.

In one embodiment, a method for determining the location of an obscured feature behind a surface comprises selecting a first mode or a second mode of an obscured feature detector, the first mode being configured to detect obscured features of a predetermined first material and the second mode being configured to detect obscured features of a predetermined second material, placing the obscured feature detector on the surface, the obscured feature detector having a plurality of sensor plates arranged in an array, and sensing the capacitance in an area surrounding one or more of the sensor plates. The method also comprises the step of identifying, based upon the sensed capacitance, the location of one or a plurality of obscured features, and activating one or a plurality of indicators to promote visual identification of the location of an obscured feature.

The step of selecting a mode may comprise selecting a wood or wood-like material mode. The step of selecting a mode may comprise selecting a metal or metal-like material mode. The set of measured capacitance values may comprise a measured reading pattern, and comparing, using the first mode, the measured reading pattern with a plurality of predetermined patterns to identify the predetermined pattern that best matches the measured reading pattern. One or more of the predetermined patterns may have capacitance values representing obscured features that comprise wood. A measured reading pattern may be defined by a set of measured capacitance values, and comparing, using the second mode, the measured reading pattern with a plurality of predetermined patterns to identify the predetermined pattern that best matches the measured reading pattern. One or more of the predetermined patterns may have capacitance values representing obscured features that comprise metal. Selecting the mode may be performed via a switch, a controller, automatically by a controller, and/or automatically after the capacitances have been measured.

In another embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the plurality of sensor plates, the sensing circuit being configured to measure the capacitance in the area surrounding each of the sensor plates, and a controller coupled to the sensing circuit, the controller being configured to analyze the capacitances measured by the sensing circuit. The controller is configured to operate in a first mode and a second mode, the first mode to detect obscured features through a first predetermined surface material, and the second mode to detect obscured features through a second predetermined surface material. The obscured feature detector further comprises one or a plurality of indicators coupled to the controller, each indicator capable of toggling between a deactivated state and an activated state, and the controller is configured to activate one or more of the indicators to identify a location of an obscured feature.

The first surface material may be wood. The second surface material may be sheetrock, concrete, and/or tile. A measured reading pattern may be defined by a set of measured capacitance values. The first mode may be configured to use a pattern matching module, the pattern matching module being configured to compare the measured reading pattern with a plurality of predetermined patterns to identify the predetermined pattern that best matches the measured reading pattern. One or more of the predetermined patterns may have capacitance values that represent a wood or wood-like surface, and/or a sheetrock or sheetrock-like surface. The mode can be selected via a switch, the controller, or automatically by the controller.

In another embodiment, a method for locating an obscured feature behind a surface comprises selecting a first mode or a second mode of an obscured feature detector, the first mode being configured to detect obscured features through a predetermined first material and the second mode being configured to detect obscured features through a predetermined second material, placing the obscured feature detector on the surface, the obscured feature detector having a plurality of sensor plates arranged in an array, sensing the capacitance in an area surrounding one or more of the sensor plates, and identifying, based upon the sensed capacitance, the location of one or a plurality of obscured features. The method further comprises the step of activating one or a plurality of indicators to promote visual identification of the location of an obscured feature.

The step of selecting a mode may comprise selecting a wood or wood-like material mode. The step of selecting a mode may comprise selecting a sheetrock or sheetrock-like material mode. A measured reading pattern may be defined by a set of measured capacitance values, and comparing, using the first mode, the measured reading pattern with a plurality of predetermined patterns to identify the predetermined pattern that best matches the measured reading pattern, and further wherein one or more of the predetermined patterns has capacitance values representing a surface material that comprises wood or metal.

In yet another embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the plurality of sensor plates, the sensing circuit being configured to measure the capacitance of each of the sensor plates, a controller coupled to the sensing circuit, the controller being configured to receive the capacitance measurements from the sensing circuit, the controller configured to operate in a first mode and a second mode, and the first mode configured to detect a single feature, and the second mode configured to be a normal operation mode. One or a plurality of indicators are coupled to the controller, each indicator capable of toggling between a deactivated state and an activated state, and the controller is configured to activate one or more of the indicators to identify a location of an obscured feature.

In another embodiment, a method for determining the location of an obscured feature behind a surface comprises selecting a first mode or a second mode of an obscured feature detector, the first mode being configured to detect a single obscured feature and the second mode being configured to be a normal mode of operation, placing the obscured feature detector on the surface, the obscured feature detector having a plurality of sensor plates arranged in an array, sensing the capacitance in an area surrounding one or more of the sensor plates, and identifying, based upon the sensed capacitance, the location of one or a plurality of obscured features. The method further comprises the step of activating one or a plurality of indicators to promote visual identification of the location of an obscured feature.

In one embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the plurality of sensor plates, the sensing circuit being configured to measure the capacitance of each of the sensor plates, a controller coupled to the sensing circuit, the controller being configured to receive the capacitance measurements from the sensing circuit, the controller configured to operate in a first mode and a second mode, and the first mode configured to detect obscured features that are at least a first distance behind a surface, and the second mode configured to detect obscured features that are less than the first distance behind the surface. One or a plurality of indicators are coupled to the controller, each indicator capable of toggling between a deactivated state and an activated state, and the controller is configured to activate one or more of the indicators to identify a location of an obscured feature.

The first distance may be ¾" or 1". A measured reading pattern may be defined by a set of measured capacitance values, the first mode configured to use a pattern matching module, the pattern matching module being configured to compare the measured reading pattern with a plurality of predetermined patterns to identify the predetermined pattern that best matches the measured reading pattern. One or more of the predetermined patterns may have values representing an obscured feature depth of at least ¾" or at least 1". More than one capacitance readings from an area may be combined to determine a value of the measured reading pattern. The first mode may combine more capacitance readings to determine a value of the measured reading pattern, and the second mode may combine fewer capacitance readings to determine a value of the measured reading pattern.

In another embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the plurality of sensor plates, the sensing circuit being configured to measure the capacitance in the area surrounding each of the sensor plates, a controller coupled to the sensing circuit, the controller being configured to receive the capacitance measurements from the sensing circuit, the controller configured to operate in a first mode and a second mode, and the first mode configured to update the indicators at a first update frequency, and a second mode configured to update the indicators at a second update frequency. One or a plurality of indicators are coupled to the controller, each indicator capable of toggling between a deactivated state and an activated state, and the controller is configured to activate one or more of the indicators to identify a location of an obscured feature.

The first update frequency may be ten indicator updates per second. The first update frequency may be twenty indicator updates per second. Multiple capacitance readings from a single area may be combined to determine a value of the measured reading pattern. The first mode may combine more capacitance readings to determine a value of the measured reading pattern, and the second mode may combine fewer capacitance readings to determine a value of the measured reading pattern. The first mode, or second mode, can be selected via an actuator. The controller may select the mode of operation. The controller may automatically select the mode. The controller may automatically select the mode after the capacitances have been measured.

In one embodiment, a method for determining the location of an obscured feature behind a surface comprises selecting a first mode or a second mode of an obscured feature detector, the first mode being configured to detect obscured features of a predetermined depth behind the surface, and the second mode being configured to detect obscured features of a predetermined second depth behind the surface, placing the obscured feature detector on the surface, the obscured feature detector having a plurality of sensor plates arranged in an array, sensing the capacitance in an area surrounding one or more of the sensor plates, identifying, based upon the sensed capacitance, the location of one or a plurality of obscured features, and activating one or a plurality of indicators to promote visual identification of the location of an obscured feature.

The step of selecting a mode may comprise selecting a deep scan mode. The step of selecting a mode may comprise selecting a shallow scan mode. A measured reading pattern may be defined by a set of measured capacitance values, and comparing, using the first mode, the measured reading pattern with a plurality of predetermined patterns to identify the predetermined pattern that best matches the measured reading pattern. One or more of the predetermined patterns may have capacitance values representing an obscured feature depth that is predetermined to be deep or shallow.

In another embodiment, a method for determining the location of an obscured feature behind a surface comprises selecting a first mode or a second mode of an obscured feature detector, the first mode being configured update the indicators at a first update frequency, and the second mode being configured to update the indicators at a second update frequency, placing the obscured feature detector on the surface, the obscured feature detector having a plurality of sensor plates arranged in an array, sensing the capacitance in an area surrounding one or more of the sensor plates, identifying, based upon the sensed capacitance, the location of one or a plurality of obscured features, and activating one or a plurality of indicators to promote visual identification of the location of an obscured feature.

In one embodiment, a method for determining the location of an obscured feature behind a surface comprises selecting a first mode or a second mode, wherein the first mode has a first feature-detection threshold, and the second mode has a second feature-detection threshold, and placing an obscured feature detector on the surface, the obscured feature detector having a plurality of sensor plates arranged in an array. The method further comprises measuring capacitance readings in an area surrounding one or more of the sensor plates, determining a disparity value defined by disparity in a set of measured capacitance readings, determining, based upon a comparison of the disparity value and the selected feature-detection threshold, whether an obscured feature is present, and activating one or a plurality of indicators to identify the location of an obscured feature.

In one embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the sensor plates, the sensing circuit being configured to measure the capacitance of each of the sensor plates, a controller coupled to the sensing circuit, the controller being configured to analyze the capacitances measured by the sensing circuit, a surface material detection module coupled to the controller and configured to detect one or more properties of a detected surface, and a correction module coupled to the controller and configured to apply corrections to the measured capacitances using at least one of the properties detected by the surface detection module.

The detected surface property may be, for example, the surface's dielectric constant, or its thickness. The detected surface property may be an estimation based on at least the surface's thickness and dielectric constant. The surface material detection module may use the smallest measured capacitance from the plurality of capacitances measured on the sensor plates to estimate a property of the surface material. The surface material detection module may measure the capacitance between two sensor plates to estimate a property of the surface material. An estimate of a property of the surface may be multiplied by a correction factor(s) to create an adjustment value(s); the adjustment value(s) may then be added to, or subtracted from, the measured capacitance(s) to correct the capacitance reading(s). A first correction factor may be applied to correct a capacitance measurement from a sensor plate that is near the edge of the detector, and a second correction factor may be applied to correct a capacitance reading from location sensor plate that is near the center of the detector. The obscured feature detector may further comprise one or a plurality of indicators coupled to the controller, each indicator may be capable of toggling between a deactivated state and an activated state, and the controller may be configured to activate one or more of the indicators to identify a location of an obscured feature. The surface material detection module may compare capacitance readings that are derived from two distinct plate activation patterns to estimate a property of the detected surface. A pattern of plate activation configurations may comprise a set of sensor plates that are floating.

In another embodiment, a method for determining the location of an obscured feature behind a surface comprises placing an obscured feature detector on the surface, the obscured feature detector having a plurality of sensor plates arranged in an array, measuring capacitance readings in an area surrounding one or more of the sensor plates, detecting at least one property of the surface, correcting the capacitance readings, using the detected property of the surface, and identifying, based upon the corrected capacitance readings, the location of one or a plurality of obscured features. The method further comprises the step of activating one or a plurality of indicators to identify the location of an obscured feature.

The step of correcting the capacitance readings may use the surface's detected dielectric constant. The step of correcting the capacitance readings may use the surface's detected thickness. The step of correcting the capacitance readings may use a detected correction factor comprising the surface's thickness and dielectric constant. Detecting a property of the surface may comprise using the one or more plates' smallest capacitance readings. Detecting a property of the surface may comprise reading the capacitance between two sensor plates. Correcting the capacitance readings may comprise multiplying the surface property by a correction factor, the product being an adjustment value, and adding or subtracting the adjustment value from the measured capacitances to correct the readings. Correcting the capacitance readings may comprise applying a first correction factor to correct a capacitance reading from a location that is near the edge of the detector, and applying a second correction factor to correct a capacitance reading from a location that is near the center of the detector. Detecting a surface property may comprise comparing readings from two different plate activation patterns to create an estimate of a surface property. Detecting a surface property may comprise reading the sensor plates with a plate activation pattern comprising a set of sensor plates that are read. Detecting a surface property may also comprise reading the sensor plates with a plate activation pattern comprising a set of sensor plates that are left floating.

In one embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to at least two of the plurality of sensor plates, and the sensing circuit being configured to measure the aggregate capacitance of at least two coupled sensor plates.

The obscured feature detector may further comprise a controller coupled to the sensing circuit, the controller may be configured to analyze the capacitances measured by the sensing circuit, and one or a plurality of indicators may coupled to the controller, each indicator capable of toggling between a deactivated state and an activated state. The controller may be configured to activate one or more of the indicators to identify a location of an obscured feature. The sensing circuit may be configured to measure the aggregate capacitance of two adjacent sensor plates. The sensing circuit may be configured to measure the aggregate capacitance of two non-adjacent sensor plates. The obscured feature detector may comprise at least four sensor plates.

In another embodiment, a method of using an obscured feature detector having a plurality of sensor plates to detect an obscured feature behind a surface comprises placing the obscured feature detector on the surface, taking a capacitance reading of at least two of the plurality of sensor plates, and transmitting said readings to a controller, identifying, based on the capacitance readings, a location of the obscured feature behind the surface, and activating one or more indicators to indicate the location of the obscured feature behind the surface.

Two adjacent sensor plates may be connected to the capacitance-to-digital converter. Two non-adjacent sensor plates may be connected to the capacitance-to-digital converter. The obscured feature detector may comprise at least four sensor plates.

In one embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a sensing circuit coupled to the sensor plates, the sensing circuit configured to measure the capacitance in the area surrounding each of the sensor plates, a controller coupled to the sensing circuit, the controller configured to analyze the capacitances measured by the sensing circuit, and one or a plurality of indicators coupled to the controller, each indicator capable of toggling between a deactivated state and an activated state. The controller is configured to detect a large obscured feature, wherein the large obscured feature is approximately at least as large as the detector, and to activate one or more of the indicators to identify a location of a large obscured feature.

The controller may be configured to detect when the detector advances over a large obscured feature, wherein the large obscured feature detection initiates as the controller senses that an obscured feature is near a group of adjacent of sensor plates, further wherein one of the sensor plates in the group of sensor plates is located at a leading end of the detector, and when the number of sensor plates in the group of sensor plates is increasing. The controller may be configured to recognize a large obscured feature by first determining that most of the sensor plates are in front of an obscured feature, and then determining that all of the sensor plates have substantially the same readings. The controller may be configured to activate all of the indicators when the entire detector is in front of an obscured feature that has a detected dimension that is at least as wide as the length of the obscured feature detector. The controller may be configured to activate all of the indicators when the entire detector is in front of an obscured feature that is approximately the size of the detector or larger, when the detector is placed over the obscured feature. The controller may be configured to determine that the detector is located in a region where a large obscured feature is present if as the detector approaches a large obscured feature all of the sensor plate readings have substantially the same capacitance value. The sensor plate readings may be above a threshold value. The sensor plate readings may have a value that is substantially similar to the value of the reading that detected an obscured feature when the detector was advancing over the large obscured feature.

In another embodiment, a method for determining the location of an obscured feature behind a surface comprises placing an obscured feature detector on the surface, the obscured feature detector having a plurality of sensor plates arranged in an array, measuring capacitance readings in an area surrounding one or more of the sensor plates, identifying, based upon the measured capacitance readings, when the detector is over a large obscured feature, and activating one or a plurality of indicators to indicate the location of an obscured feature.

A first set of measured capacitive readings from a first time period and a second set of measured capacitive readings from a second time period may be used to identify when the detector is over an obscured feature. A first set of measured capacitive readings from a first time period and a second set of measured capacitive readings from a second time period may be used to identify when the detector is over an obscured feature and wherein when the capacitive readings from the second time period may be sufficiently proximate to the capacitive readings from the first time period then the controller identifies the region as one where an obscured feature is present. A first set of measured capacitive readings from a first time period and a second set of measured capacitive readings from a second time period may be used to identify when the detector is over an obscured feature and wherein values from the first time period may be compared to the values from the second time period only if the controller identified the respective region as one where an obscured feature was present during the first time period. All of the indicators may be activated when the detector is over an obscured feature that is at least approximately as wide as the length of the detector. A first set of measured capacitive readings from a first time period and a second set of measured capacitive readings from a second time period may be used to identify when the detector is over an obscured feature, and wherein the detector may determine that the detector may be near a large obscured feature in the first time period. A first set of measured capacitive readings from a first time period and a second set of measured capacitive readings from a second time period may be used to identify when the detector is over an obscured feature, and wherein the detector may determine that the detector may be near a large obscured feature in the first time period, and wherein the detector may determine that each of the measured capacitive readings are substantially similar in the second time period.

In another embodiment, an obscured feature detector comprises a plurality of sensor plates, each having a capacitance that varies based on: (a) the proximity of the sensor plates to one or more surrounding objects, and (b) the dielectric constant(s) of the surrounding object(s). The obscured feature detector further comprises a multiplexer connecting at least one of the sensor plates to a sensing circuit, and the sensing circuit is configured to measure the capacitance of each of the sensor plates. A controller is coupled to the sensing circuit, the controller is configured to analyze the capacitances measured by the sensing circuit, and one or a plurality of indicators is coupled to the controller, each indicator capable of toggling between a deactivated state and an activated state. The controller is configured to activate one or more of the indicators to identify a location of an obscured feature.

The multiplexer may connect a single sensor plate to the capacitance-to-digital converter. The multiplexer may connect more than one sensor plate to the capacitance-to-digital converter. The multiplexer may connect more than one non-adjacent sensor plate to the capacitance-to-digital converter. The multiplexer may be configured so that the sensing circuit measures the capacitance of one sensor plate. The multiplexer may be configured so that the sensing circuit measures the aggregate capacitance two or more sensor plates. The obscured feature detector may comprise at least four sensor plates.

In another embodiment, a method for determining the location of an obscured feature behind a surface comprises placing an obscured feature detector on the surface, the obscured feature detector having a plurality of sensor plates arranged in an array, transmitting a capacitance reading from at least one of the sensor plates to a controller, wherein the capacitance reading comprises the capacitance in an area surrounding the at least one sensor plate, and identifying, based upon the capacitance readings, the location of one or more obscured features.

The method may further comprise activating one or more indicators to indicate the location of an obscured feature. The obscured feature detector may comprise at least four sensor plates. Two adjacent sensor plates may be electrically connected to the sensing circuit. And two non-adjacent sensor plates may be electrically connected to the sensing circuit.

A novel and non-obvious feature of the obscured feature detector is the ability to instantly identify the location of multiple objects simultaneously.

A novel and non-obvious feature of the obscured feature detector is the ability to identify the width of obscured features.

A novel and non-obvious feature of the obscured feature detector is the ability to provide more reliable readings. The detector uses the information from multiple sensor plates' readings to determine the location of obscured features; as a result the detector is less susceptible to signal noise because more sensor readings are used to determine the location of obscured features, making the detector less dependent upon any single reading.

A novel and non-obvious feature of the obscured feature detector is the ability to properly identify the location of features. In particular, other detectors may be less effective at properly identifying the positions features, particularly when two features are relatively close. When two features are relatively close, the highest capacitive readings may be detected at the location that is between the two features, other detectors may incorrectly identify this as the location of an obscured feature. The obscured feature detector can properly identify the location of multiple features in close proximity.

A novel and non-obvious feature of the obscured feature detector is the ability to create a detector that is easy to use. The user may only need to press a button and place it on a surface to identify the location of obscured features. Prior art detectors tend to require more steps, and more proficiency to determine the location of obscured features.

A novel and non-obvious feature of the obscured feature detector is the ability more accurately detect obscured features through materials with inconsistent densities. Construction materials may have density inconsistencies. Because the obscured feature detector has the ability to use the information from multiple sensors to determine the location of obscured features, errors in readings due to inconsistencies in the material have less effect on the detector's ability to identify the location of features.

A novel and non-obvious feature of the obscured feature detector is the ability to detect features more deeply and to more accurately determine the position of obscured features. The detector can combine information from multiple sensor plates to determine the location of obscured feature(s). The use of more information provides higher quality interpretation of the detected features and may be able to detect more deeply.

A novel and non-obvious feature of the surface-conforming obscured feature detector is the capability to create larger detectors.

The present disclosure will now be described more fully with reference to the accompanying drawings, which are intended to be read in conjunction with both this summary, the detailed description, and any preferred or particular embodiments specifically discussed or otherwise disclosed. This disclosure may, however, be embodied in many different forms and should not be construed as limited to the embodiments set forth herein; rather, these embodiments are provided by way of illustration only so that this disclosure will be thorough, and fully convey the full scope of the invention to those skilled in the art.

BRIEF DESCRIPTION OF THE DRAWINGS

In FIG. 7 four sensor plates are also illustrated.

In FIG. 13 there are also four curves that illustrate four different predetermined patterns.

FIG. 14 is a table showing an example of the calculation of the score using a slope-based scoring method.

FIG. 15 is a table showing an example of the calculation of the score using another slope-based scoring method.

FIG. 16 is a perspective view of one embodiment of an obscured feature detector configured to detect large obscured features.

Figure 1:
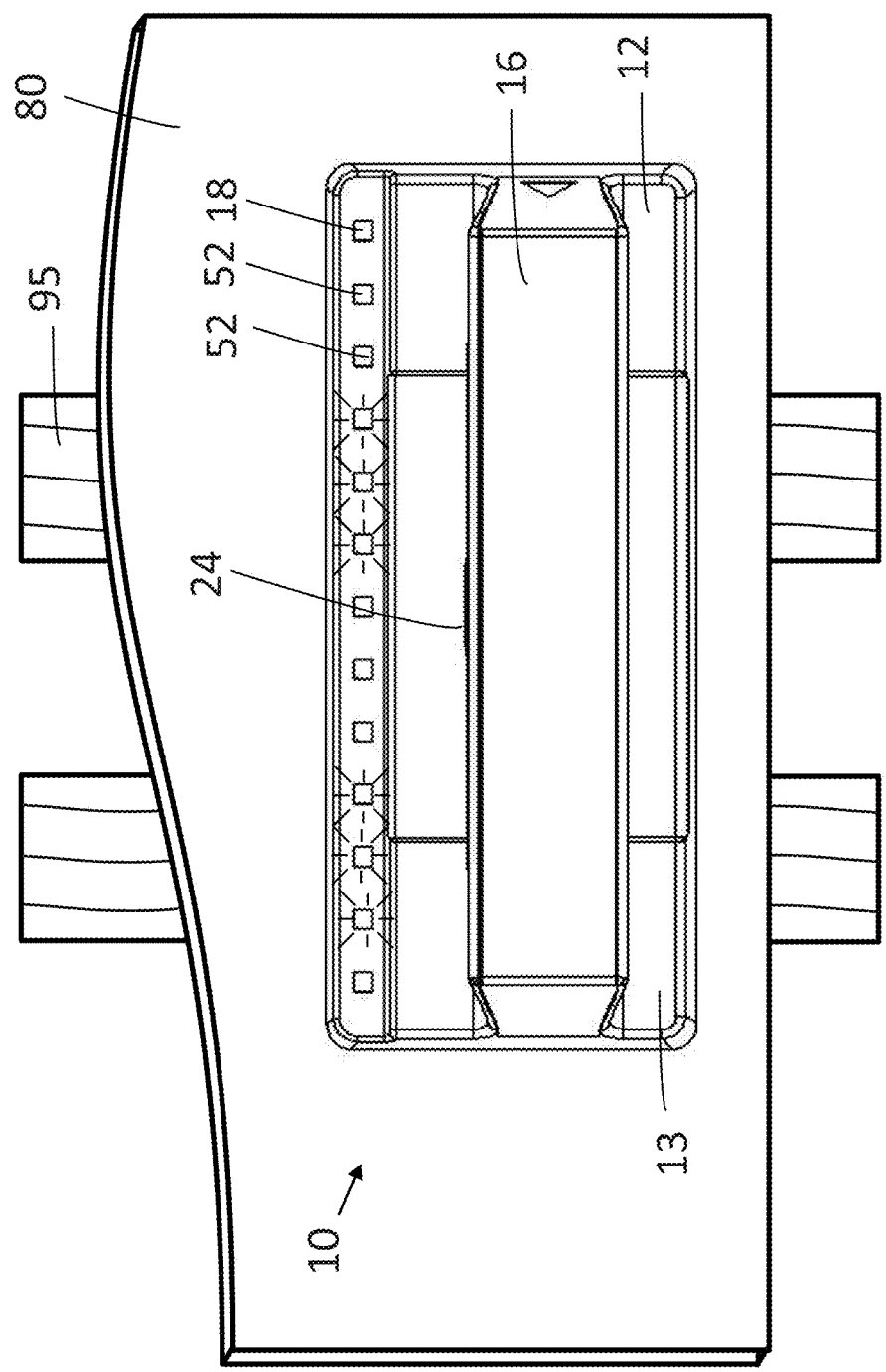
FIG. 1 illustrates one embodiment of an obscured feature detector that is being used on one particular surface with two obscured features. The two obscured features in this example are studs. In front of the studs there is a surface material. On top of the surface material there is an obscured feature detector. In this example, the indicators that are in front of the obscured features are illuminated to indicate the locations of the detected obscured features.

In the following description, reference is made to the accompanying drawings that form a part thereof, and in which is shown by way of illustration specific exemplary embodiments in which the invention may be practiced. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

DETAILED DESCRIPTION

To provide context for the disclosure it may be useful to understand how capacitance is used to detect obscured features behind a surface. Capacitance is an electrical measure of an object's ability to hold or store charge. A common form of an energy storage device is the parallel plate capacitor whose capacitance is calculated by: $C = \in_r \in_o A/d$, where A is the overlapping area of the parallel plates, d is the distance between the plates and $\in_r$ is the relative static permittivity, or dielectric constant of the material between the plates, $\in_o$ is a constant. The dielectric constant ($\in_r$) of air is one, while most solid non-conductive materials have a dielectric constant greater than one. Generally, the increased dielectric constants of non-conductive solids enable conventional capacitive displacement sensors to work.

In their most rudimentary form, capacitive sensors are in part single-plate capacitive sensors. These single-plate capacitive sensors use the environment surrounding them as the dielectric where the second plate can be assumed to be infinitely far away. The plates will also form capacitors with other metal plates. When two plates are positioned against a wall, they are not facing each other as is suggested by the definition of a capacitor. Nonetheless, the stray fields emanating from the edges of each of the adjacent plates do extend into the wall and behind it, and curve back to an adjacent plate, forming a capacitor.

When the plates are placed on a wall at a location with no support behind the wall, the detector 10 measures the capacitance of the wall and the air behind it. When placed in a position having a support behind the wall, the detector 10 then measures the capacitance of the wall and the support, which has a higher dielectric constant than air. As a consequence, the detector 10 registers an increase in capacitance which can then be used to trigger an indicating system.

This description of feature sensing through capacitive sensing is provided in order to facilitate an understanding of the disclosure. Persons of skill in the art will appreciate that the scope and nature of the disclosure is not limited by the description provided.

The present disclosure is directed to an obscured feature detector 10. In the exemplary embodiments illustrated in FIGS. 1, 2, 3, 4, and 6 the obscured feature detector 10 comprises a sensor plate array 31 (see FIG. 7), a multi-layer printed circuit board 40 (see FIGS. 2, 3, and 6), a sensing circuit 30 (see FIG. 4), a controller 60 (see FIGS. 4, 5), a display circuit 50 (see FIG. 4), a plurality of indicators 52 (see FIGS. 1, 3, 4, and 6), a power controller 20 (see FIG. 4), and a housing 12 (see FIGS. 1, 2, 3, and 6).

Figure 7:
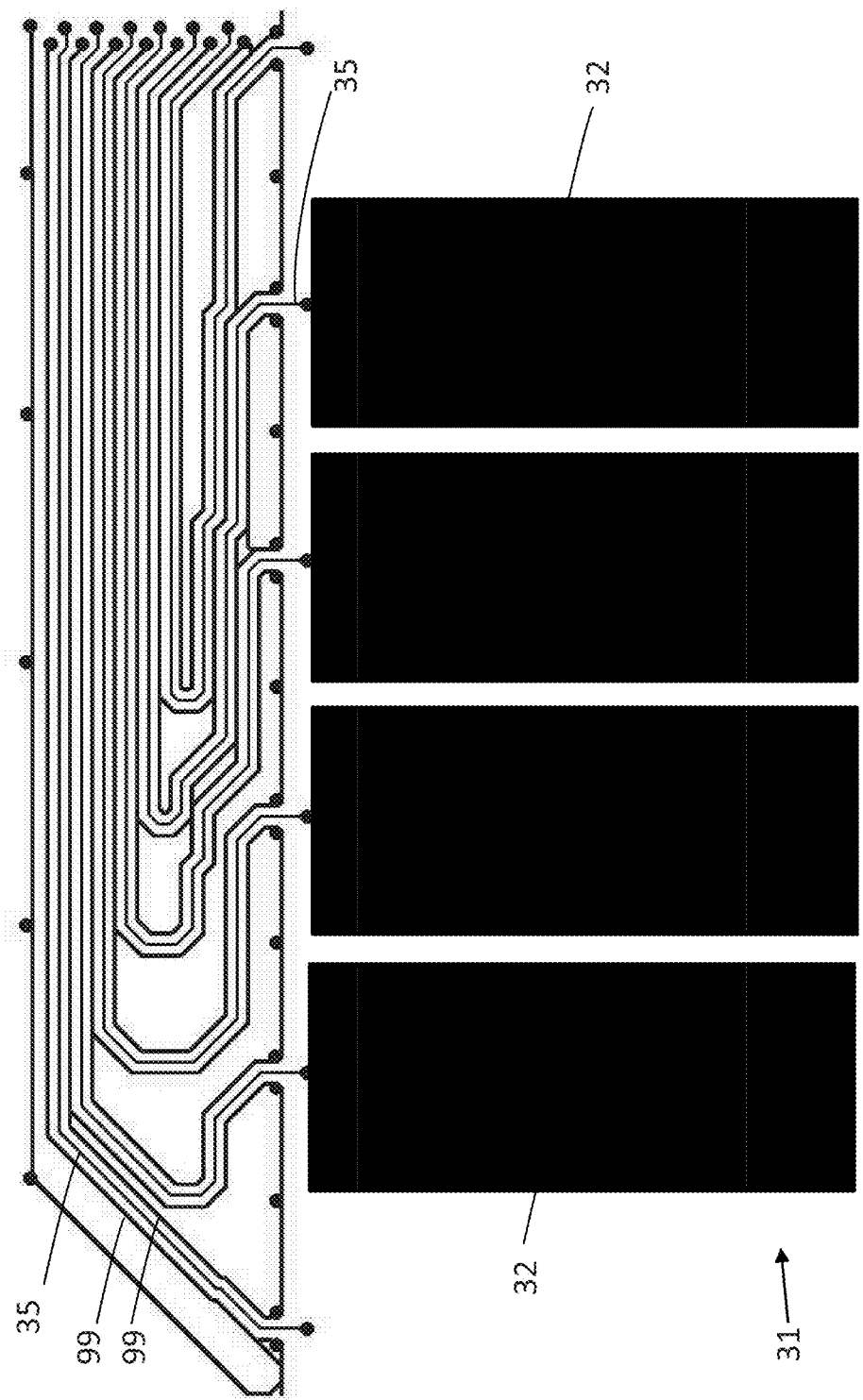
FIG. 7 illustrates a method of routing the several sensor plate traces, used in some embodiments. In this method all of the sensor plate traces have the same length. All of the sensor plate traces are also uniformly shielded on both sides.

In some embodiments, as shown in FIG. 7, the sensor plate array 31 comprises two or more sensor plates 32 arranged substantially in a plane. Each sensor plate 32 has a capacitance that varies based on: (a) the proximity of the sensor plate 32 to one or more surrounding objects, and (b) the dielectric constant(s) of the surrounding object(s). Thus, by evaluating the capacitances of the sensor plates 32, the sensor plate array 31 is capable of sensing the presence and location of one or more features obscured by a surface (see FIG. 1) in contact or proximity with the obscured feature detector 10. In some embodiments each of the sensor plates 32 are substantially the same size.

The sensor plates 32 can be positioned side by side in a linear arrangement so that a longitudinal axis of the array 31 is substantially perpendicular to a longitudinal axis of the individual sensor plates 32. In some embodiments, the obscured feature detector 10 comprises thirteen sensor plates 32, with a gap of approximately 1.7 mm between adjacent plates. In some embodiments, each sensor plate 32 has a width of about 11 mm wide and a length of about 47 mm. The individual plates 32 can comprise thin, conductive surfaces and can be manufactured using a variety of suitable techniques, such as, for example, depositing conductive ink on a substrate or applying thin sheets of conductive material to the substrate.

Figure 6:
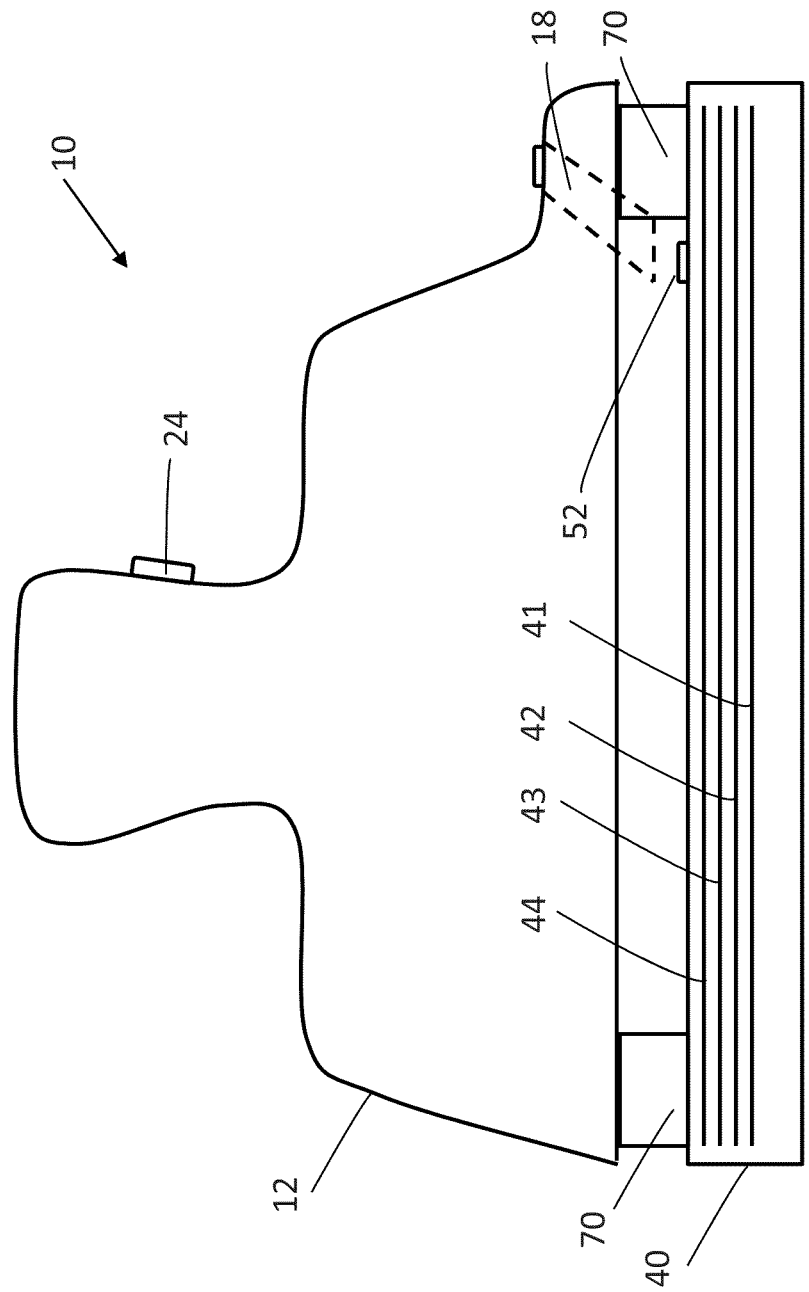
FIG. 6 is a cross sectional view of an embodiment of an obscured feature detector.

In some embodiments, each individual sensor plate 32 of the sensor plate array 31 can be independently connected to the capacitance-to-digital converter 38 via a multiplexer 37 (see FIG. 4), and the sensor plate array 31 itself is attached to a layer 41 of the printed circuit board 40, the printed circuit board 40 being positioned on the underside of the detector 10 (see FIG. 6). In some embodiments, the obscured feature detector 10 has at least four sensor plates 32, which advantageously enables the obscured feature detector 10 to detect the full width of a common obscured feature, such as a stud 95, from a stationary position. By contrast, many existing stud detectors with fewer than four sensor plates 32 cannot detect the full width of a stud 95 without being moved.

In some embodiments, as shown in FIG. 6, the printed circuit board 40 comprises a multi-layer board with a layer comprising a sensor board 41 on which the sensor plate array 31 and other electrical traces are placed, one layer comprising a ground plane board 43 upon which a ground plane and other electrical traces are placed, a power plane board 42 upon which a power plane and other electrical traces are placed, and a top layer comprising a metal shielding 44, and other electrical traces. In some embodiments the sensor plate array 31 is placed on an internal layer of the printed circuit board 40 which may protect the circuits from some electrostatic discharge. Placing the sensor plates 32 on an internal layer may also minimize the expansions and contractions of the sensor plates 32 as the printed circuit board 40 is flexed. Sensor plates 32 that do not expand and contract with flexing may provide more consistent readings. In some embodiments the electrical traces comprise electrically conductive paths.

The printed circuit board 40 can be made from a variety of suitable materials, such as, for example, FR-4, FR-406, or more advanced materials used in radio frequency circuits, such as Rogers 4003C. Rogers 4003C, and other radio-frequency-class printed circuit board substrates, may offer improved performance across a broader temperature range. In the embodiment illustrated in FIG. 6, the printed circuit board 40 is positioned external to the housing 12.

Figure 4:
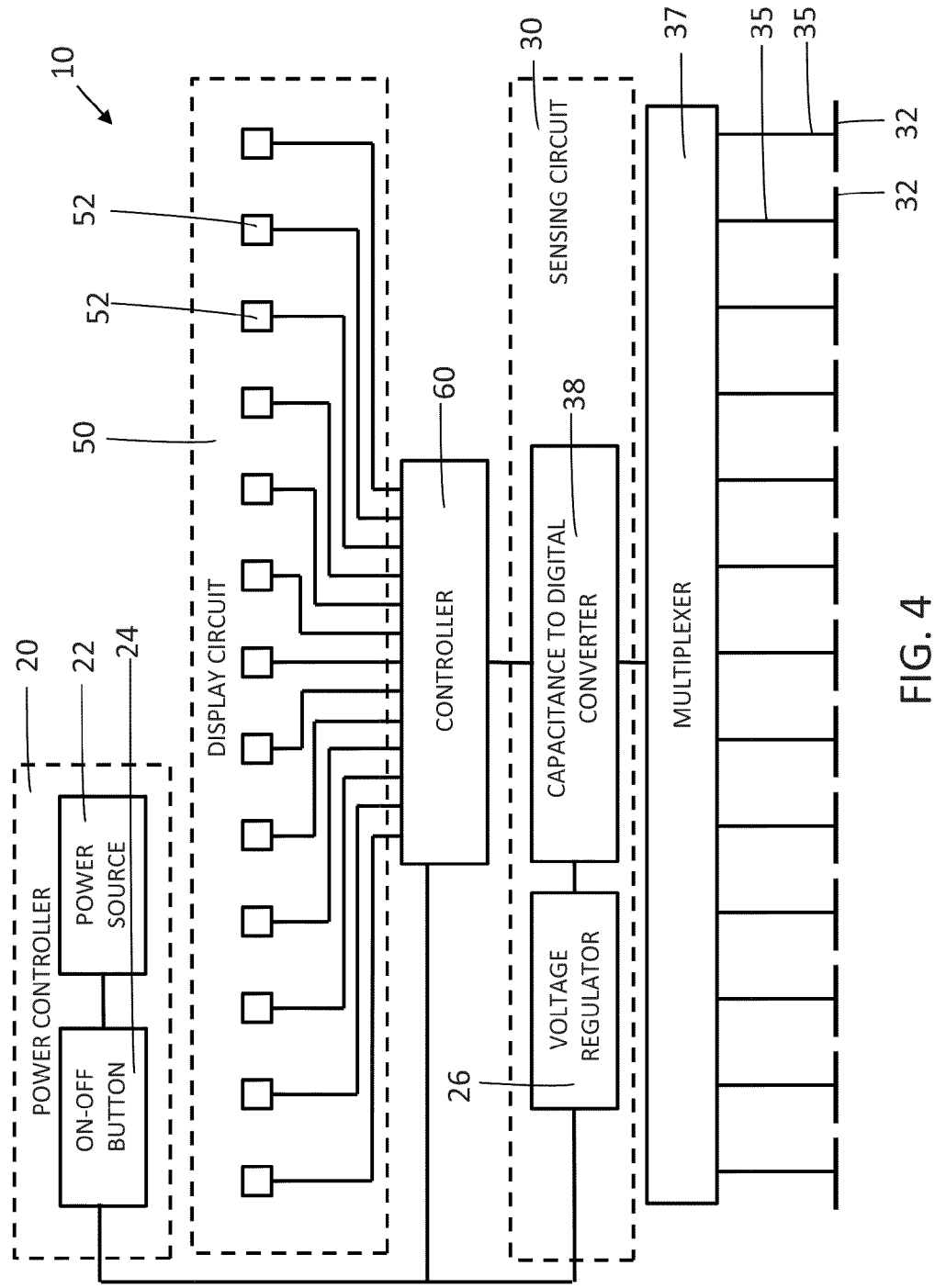
FIG. 4 is a block diagram that represents certain functional components of one embodiment of an obscured feature detector.

In some embodiments, as shown in FIG. 4, the sensing circuit 30 comprises a plurality of sensor a voltage regulator 26, and a capacitance-to-digital converter 38. The sensing circuit 30 can be connected to the controller 60. The sensor plate traces 35 can comprise electrically conductive paths on the printed circuit board 40, which may connect the individual sensor plates 32 to the capacitance-to-digital converter 38, the connection being made via the multiplexer 37. The multiplexer 37 can individually connect the sensor plates 32 to the capacitance-to-digital converter 38.

In some embodiments the multiplexer 37 may connect and single sensor plate 32 to the sensing circuit. In some embodiments, the multiplexer 37 may connect more than one adjacent sensor plates 32 to the sensing circuit. In some embodiments, the multiplexer 37 may connect more than one non-adjacent sensor plates 32 to the sensing circuit. In some embodiments, the multiplexer 37 is configured so that the sensing circuit measures the capacitance of one sensor plate 32. In some embodiments, the multiplexer 37 is configured so that the sensing circuit measures the aggregate capacitance two or more sensor plates 32.

As used herein, the term "module" can describe any given unit of functionality that can perform in accordance with one or more embodiments of the present invention. For example, a module might by implemented using any form of hardware, software, or a combination thereof, such as, for example, one or more processors, controllers 60, ASICs, PLAs, logical components, software routines, or other mechanisms.

Figure 5:
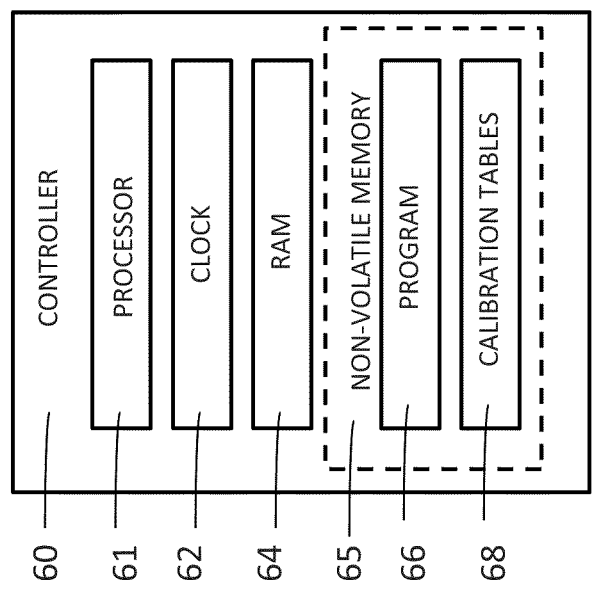
FIG. 5 is a block diagram of a controller suitable for use with an obscured feature detector.

In some embodiments, as shown in FIG. 5, the controller 60 comprises a processor 61, a clock 62, a random access memory (RAM) 64, and a non-volatile memory 65. In operation, the controller 60 receives program code 66 and synchronizes the functions of the capacitance-to-digital converter 38 and the display circuit 50 (see FIG. 4). The non-volatile memory 65 receives and holds the programmable code 66 as well as look-up tables (LUT) and calibration tables 68. The program code 66 can include a number of suitable algorithms, such as, for example, an initialization algorithm, a calibration algorithm, a pattern-matching algorithm, a multiplexing algorithm, a display management algorithm, an active sensor activation algorithm, and a non-active sensor management algorithm.

The capacitance-to-digital conversion process can be accomplished by the AD7147 from Analog Devices. Other integrated circuits that can be used to perform the capacitance-to-digital conversion include the AD7477 from Analog Devices, the CY8C21534 from Cypress Semiconductor, the C8051CF706 from Silicon Laboratories, or others. The voltage regulator 26 may comprise the ADP150-2.8 from Analog Devices which provides very low noise. The controller 60 may comprise the C8051F543 from Silicon Laboratories, or any of many other microcontrollers.

Figure 2:
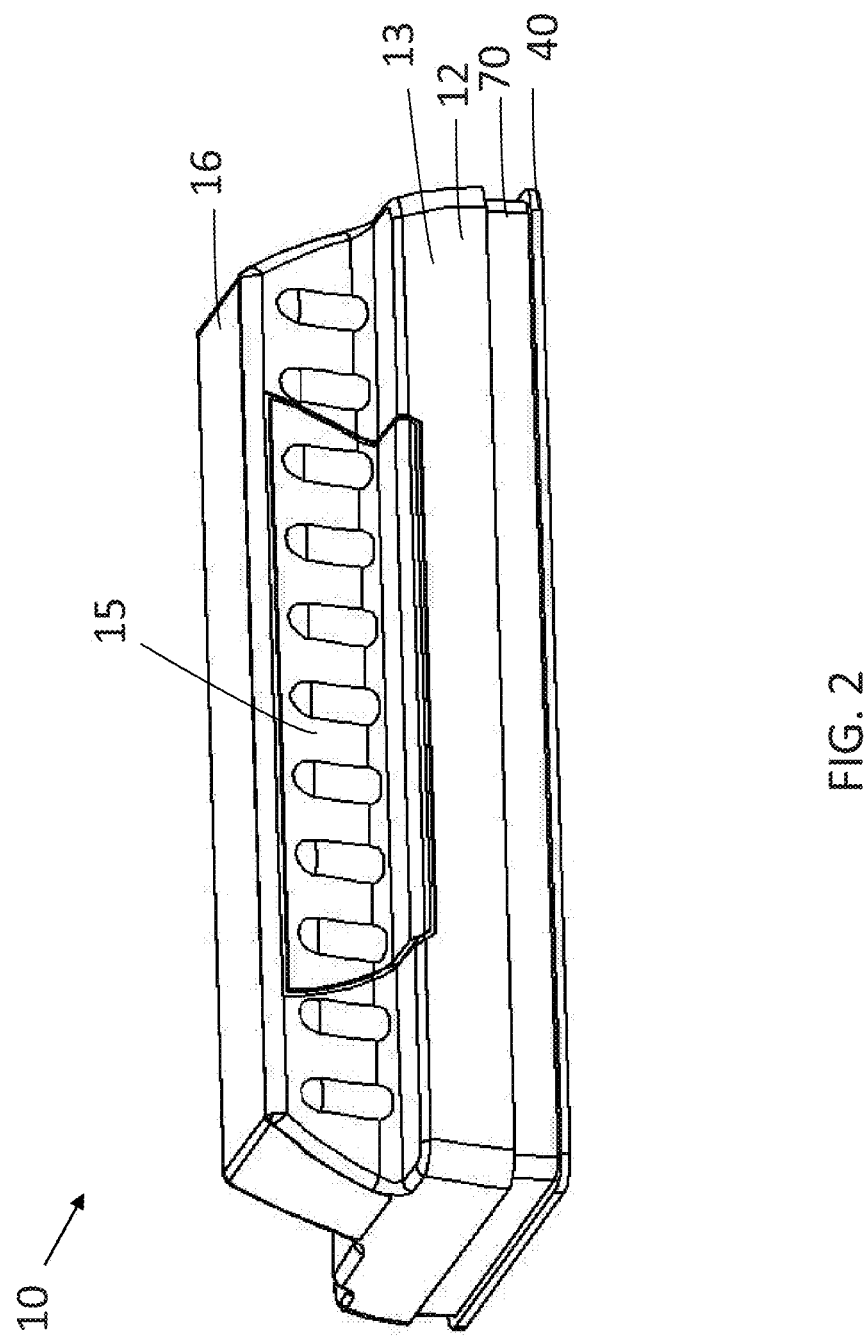
FIG. 2 is a perspective view of one embodiment of an obscured feature detector.
Figure 3:
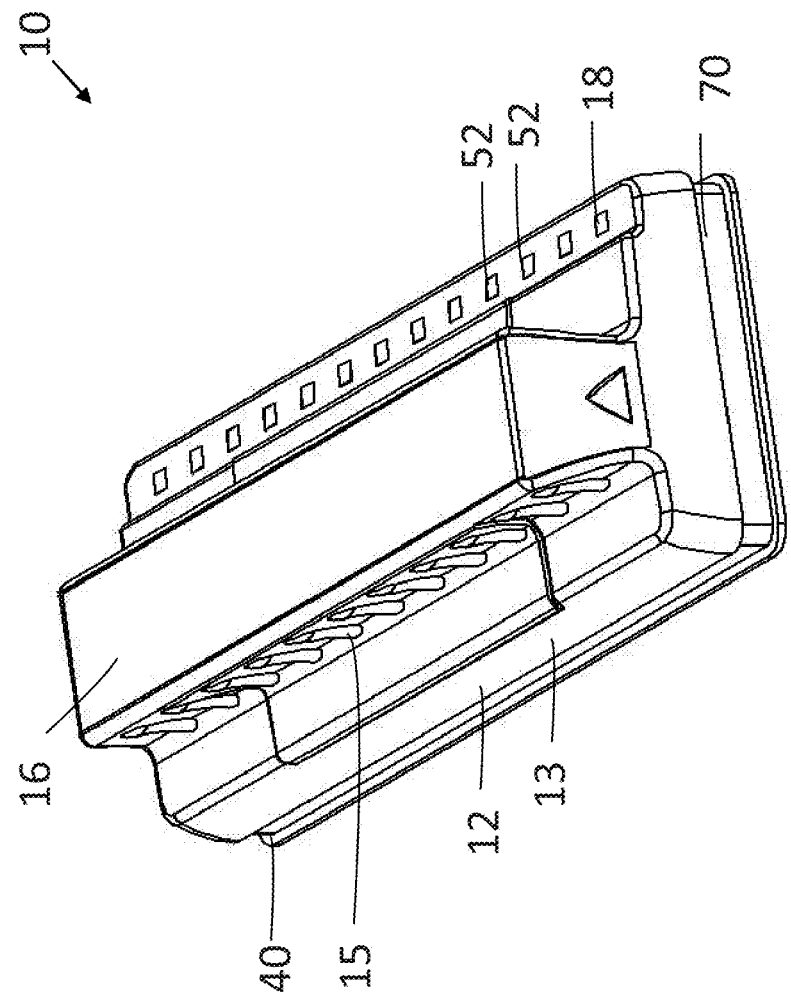
FIG. 3 is a perspective view of one embodiment of an obscured feature detector.

In some embodiments, as shown in FIGS. 2, 3, and 6 the housing 12 comprises an upper housing 13, an on/off switch 24, a handle 15, a plurality of light pipes 18, and a power supply compartment 16. In some embodiments the underside of the housing 12 is attached to a first side of a foam ring 70. In some embodiments the foam ring 70 is made of non-conductive EPDM foam rubber. In some embodiments the foam ring 70 is attached to the housing 12 using a pressure sensitive acrylic adhesive. In some embodiments the foam ring 70 is attached to the printed circuit board 40 using a pressure sensitive acrylic adhesive. In some embodiments the multi-layered printed circuit board 40, contains the capacitance-to-digital converter 38, the display circuit 50, and the controller 60. In some embodiments, the upper housing 12 comprises plastic. In some embodiments, the upper housing 12 comprises ABS plastic.

In some embodiments, the handle 15 comprises a gripping surface. In some embodiments a portion of the gripping surface comprises an elastomer. In some embodiments the gripping surface is positioned such that when the detector 10 is held on a wall in a position to detect a vertical feature, such as a vertical stud 95, the handle 15 is substantially horizontal or substantially perpendicular to the vertical stud 95. In some embodiments the gripping surface that is oriented such that when the detector 10 is held on a wall in a position to detect vertical studs 95, two or more fingers are lined up with an orientation that is more horizontal than vertical. In some embodiments the gripping surface is a curved surface. In some embodiment the gripping surface is a substantially flat surface.

The handle 15 is preferably positioned so that the user's hand does not obscure the view of the indicators 52 when grasping the handle 15. In some embodiments, the power supply compartment 16 comprises a cavity for holding a suitable power supply, such as batteries, and a cover for accessing the compartment 16.

In order to accommodate the thirteen sensor plates 32, the housing 12 can have a length of about seven inches and a width of about three inches. A handle 15 running along the longitudinal axis of the upper housing 13 can be designed to be easy to hold while keeping the user's hand about one inch away from the surface of the PCB 40 and at the same time not obscuring the user's line of sight to the rows of indicators 52 positioned on the back side of the upper housing 13. In some embodiments the indicators 52 are LEDs (Light Emitting Diodes). In other embodiments, the user's hand may be less than one inch away from the surface of the printed circuit board 40

In some embodiments, as shown in FIG. 4, the obscured feature detector 10 comprises a power controller 20 having a power source 22, an on-off switch 24, and a voltage regulator 26. The power source 22 can comprise an energy source for powering the indicators 52, and supplying power to the capacitance-to-digital converter, and the controller 60. In some embodiments, the power source 22 can comprise a DC battery supply. The on-off switch 24 can be used to activate controller 60 and other components of the obscured feature detector 10. In some embodiments, the on-off switch 24 comprises a push button mechanism that activates components of the obscured feature detector 10 for a selected time period. In some embodiments the push button activates the components such that the components remain activated until the button is released. In some embodiments the on-off switch 24 comprises a capacitive sensor that can sense the presence of a finger, or thumb over the button. In some embodiments, the on-off switch 24 can comprise a toggle switch, or other types of buttons or switches. The voltage regulator 26 may be used to condition the output of the power controller 20, as desired. In some embodiments a voltage regulator 26 is placed as near as possible to the capacitance-to-digital converter 38, which may provide a better power source 22 to the capacitance-to-digital converter 38.

Different processes of reading a capacitance and converting it to a digital value, also known as a capacitance-to-digital conversion, are well-described in the prior art. The many different methods are not described here, the reader is referred to the prior art for details about different capacitance-to-digital converter methods. Some embodiments use a sigma-delta capacitance-to-digital converter 38, such as the one that is built into the Analog Devices AD7147 integrated circuit. Some embodiments use a charge-sharing method of capacitance-to-digital conversion.

Figure 8:
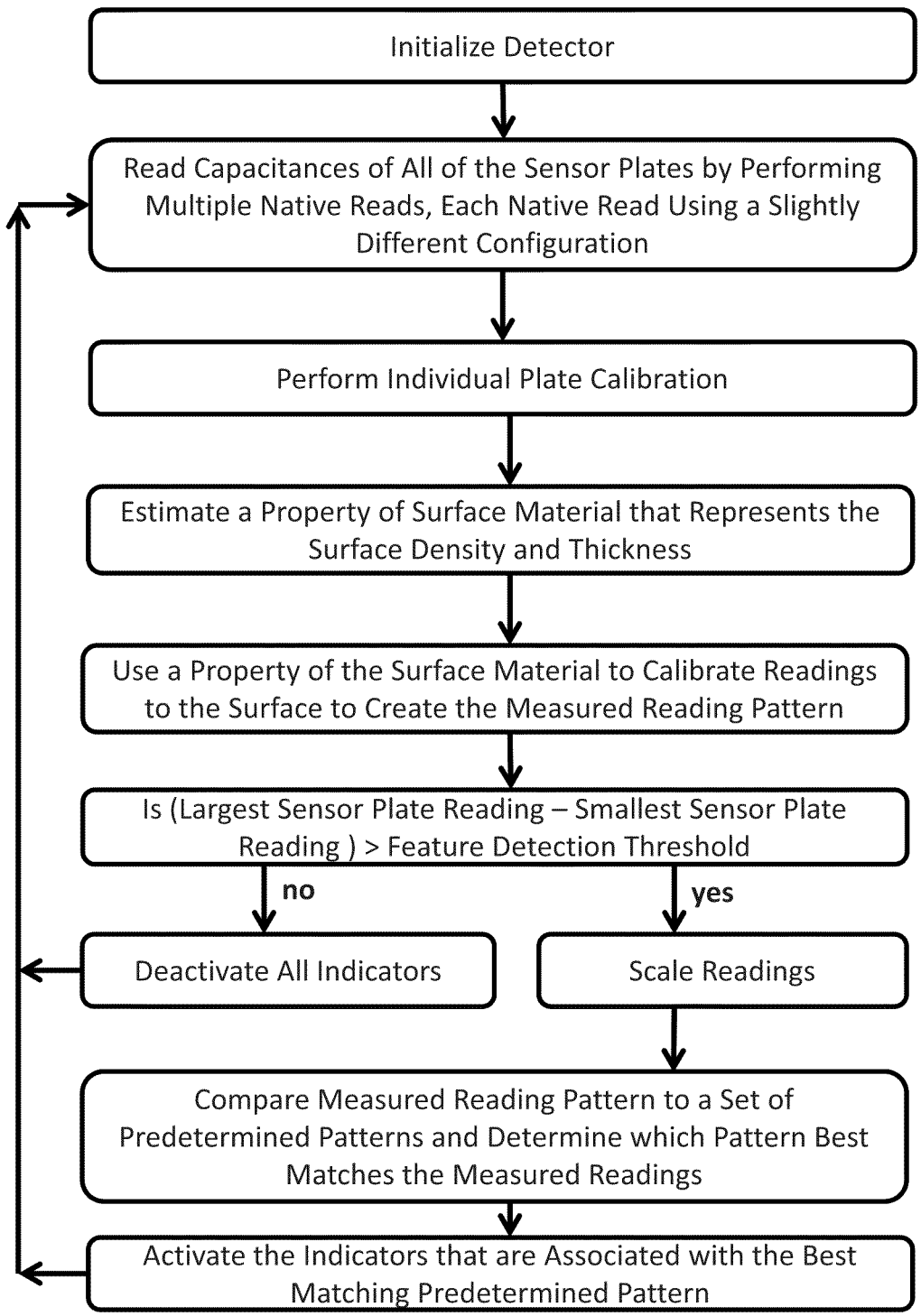
FIG. 8 is a flow diagram showing a feature detection process implemented in some embodiments of an obscured feature detector.

FIG. 8 is a flow diagram showing a feature detection process 200 implemented in some embodiments of the obscured feature detector 10. The detection process 200 begins with a first step 202, in which the obscured feature detector 10 is initialized. In some embodiments, initialization occurs automatically after the obscured feature detector 10 is turned on. Upon initialization, some embodiments immediately perform a set of capacitance-to-digital conversions to "warm-up" the circuitry. Next the sensor plates 32 are read.

Detecting obscured features can require a high degree of accuracy, and may require more accuracy than a capacitance-to-digital converter 38 may able to provide, if the native capacitance-to-digital converter readings are used alone. Native readings are the raw values read from the capacitance-to-digital converter 38, they are the digital output of the capacitance-to-digital converter 38.

Some embodiments perform native reads multiple times, and combine the results of the multiple native reads, to create a reading. Some embodiments perform native reads multiple times, and combine the results of the multiple native reads, using a different configuration for two or more of the native reads to create a reading. Some embodiments perform native reads multiple times, and sum or average the results of the multiple native reads, to create a reading. In some embodiments this improves the signal to noise ratio. Each native read may involve reading one sensor plate 32. A native read could also involve reading a plurality of sensor plates 32, if multiple sensor plates 32 are multiplexed to the capacitance-to-digital converter 38. In the some embodiments multiple native reads are combined to create a reading.

Summing or averaging multiple native reads may improve the signal to noise ratio, but it may not reduce the effect of non-linearities in the capacitance-to-digital converter 38. An ideal capacitance-to-digital converter 38 is perfectly linear, which means that its native readings increase in direct proportion to an increase in the capacitance being sensed. However, many capacitance-to-digital converters 38 may not be completely linear, such that a change in the input capacitance doesn't result in an exactly proportional increase in the native reading. These non-linearities may be small, but when a high degree of accuracy is desired it may be desirable to implement methods that reduce the effects of the non-linearities.

In some embodiments, the ill effects of the non-linearities may be mitigated by summing multiple native reads, using a slightly different configuration for each of the native reads. Some embodiments perform native reads using two or more different configurations. For example, the AD7147 from Analog Devices has a capacitance-to-digital converter 38, which may be used by some embodiments. The AD7147 offers a few different parameters that can be set in different ways to create different configurations.

For example, with the AD7147, the bias current is one of the parameters that can be altered to create different configurations. The bias current could be set to normal, or normal +20%, or normal +35%, or normal +50%. Different bias currents produce different native readings, even if all other factors remain constant. Since each native reading has a different value, presumably each native reading may be subject to different non-linearities. Presumably summing or averaging readings that are subject to different non-linearities may cause the non-linearities to partially cancel each other out, instead of being summed, or multiplied.

The AD7147 chip also has two separate and independent capacitance-to-digital converters 38. Presumably each of them may have different non-linearities. By using both of the capacitance-to-digital converters 38, using a first converter for some of the reads, and using the second converter for some of the reads, may mitigate the effect of any single non-linearity.

The AD7147 capacitance-to-digital converter 38 also offers a differential connection to the capacitance-to-digital converter 38, or a single ended connection to the capacitance-to-digital converter 38. Both connections can be used for single ended reads, but each connection method provides results with different values. Doing some reads with a first capacitance-to-digital converter 38, and some reads with a second capacitance-to-digital converter 38, and summing the results, may mitigate the effect of any single non-linearity.

Some embodiments perform native reads on each of thirteen sensor plates 32 using each of twelve different configurations. Therefore, to read each of thirteen sensor plates 32 twelve times each requires one hundred and fifty six native reads. Other embodiments may use other parameters to created different configurations.

After completing the readings, in some embodiments, two different calibration algorithms may be performed: first an individual-plate calibration that adjusts for individual sensor plate 32 variations, and second a surface material calibration that adjusts the readings so that they are tuned to the surface density/thickness. Other embodiments may only use one of the two calibration algorithms. Some embodiments may use other calibration algorithms. In some embodiments the calibration algorithms are performed by a calibration module.

In some embodiments, individual plate calibration is employed first. With individual plate calibration, each sensor may have its own individual calibration value. In some embodiments, after the readings are taken, an individual plate calibration value is added to, or subtracted from, each of the readings. Other embodiments may use multiplication, or division, or other mathematical functions to perform the individual plate calibration. In some embodiments, the individual plate calibration value is stored in non-volatile memory. Individual plate calibration compensates for individual sensor plate 32 irregularities, and is used to compensate for these irregularities. It is presumed that after performing individual plate calibration that the readings will presumably have the same calibrated values, if the sensor plate readings are taken while the detector 10 is on a surface that is similar to the surface the detector 10 was calibrated with. For example, if readings are performed on ½" sheetrock 80, without any obscured features present, and the individual calibration values were created for ½" sheetrock 80, then after performing individual plate calibration, it is presumed that all the readings would be corrected to a common value. If readings are performed on a thicker material (such as ⅝" sheetrock 80), or thinner material (such as ⅜" sheetrock 80), or a different material (such as ¾" plywood) then there may be some error in the values. Surface material calibration may help correct this error.

In some embodiments surface material calibration may be used in part because the sensor plates 32 near the center of the detector 10 may have capacitive coupling with adjacent sensor plates 32 on both sides, whereas sensor plates 32 near the end of the detector 10 may only have capacitive coupling with adjacent sensor plates 32 on one side. The value of these capacitors may differ, depending on the thickness and density of the surface material. In some embodiments the sensor plates 32 near the ends of the detector 10 may be more sensitive to the thickness and density of the material being tested than the plates near the center.

To better explain this phenomenon by way of example, suppose that the detector 10 is placed on a sheet of ½" sheetrock 80 without any obscured features present and the detector 10 is calibrated such that all of the readings are adjusted such that they all read a common value, such as 0. Next the detector 10 is placed on the surface of another material that is has a higher dielectric constant, such as ½" MDF (medium density fiberboard). The readings from the sensor plates 32 that are near center of the detector may now read a value of 80, while the readings from the sensor plates 32 that are near the edge of the detector 10 may now read a value of 110. Thicker and denser materials may cause more change to readings from sensor plates 32 near the edge of the detector than to readings from sensor plates 32 near the center of the detector.

To compensate, some embodiments use a surface material estimation module, so that compensation can be made to minimize this effect. The surface material estimation module estimates a property that can be used to correct this error. The surface material estimation module may estimate a property of the surface material. In some embodiments a higher property value coincides with a material has a greater effect on the pads near the edges, than on the pads near the center. The surface material property in some embodiments is a one value parameter; higher values may correspond to a thicker and denser surface. Some embodiments may use multiple properties to estimate properties of the surface material.

In some embodiments, the dielectric constant of the surface is a property of the surface that is estimated by the surface material detection module. In some embodiments, the thickness of the surface is a property of the surface that is estimated by the surface material detection module. In some embodiments, the property of the surface that is estimated is a factor that is comprised of a combination of the thickness of the surface material, and dielectric constant of the surface material. In some embodiments the surface detection module uses the smallest measured capacitance to estimate a property of the surface material.

Presumably, the smallest measured capacitance reading may correspond to a surface that does not have an obscured feature behind it. The smallest measured capacitance reading may provide a good estimate of surface material property. In some embodiments, where the detector 10 is only intended for one type of material (such as only sheetrock 80) this may be sufficient.

In some embodiments, a surface material property can be estimated by creating a dual-plate capacitor between adjacent sensor plates 32 and reading the value of the capacitor. This may be accomplished in some embodiments by reading the value of a sensor plate 32, while one or both of the adjacent sensor plates 32 are grounded.

In some embodiments two different patterns of plate activation configurations are compared to create an estimate of a property of a surface. In some embodiments a pattern of plate activation configurations comprises a set of sensor plates 32 that are read. In some embodiments a pattern of plate activation configurations comprises a set of sensor plates 32 that are floating. In some embodiments a pattern of plate activation configurations comprises a set of sensor plates 32 that are driven at a constant voltage. In some embodiments a pattern of plate activation configurations comprises a set of sensor plates 32 that are driven as active shields. Active shields are driven with a voltage that is similar to the voltage that is driven on the sensor plates 32 that are being read. In some embodiments a pattern of plate activations configurations comprises a set of sensor plates 32 that are read, and a set of sensor plates 32 that are floating.

In some embodiments, including the embodiments that use the Analog Devices AD7147 integrated circuit, each of the individual sensor plates 32 can be activated in any of at least three different ways (1) as actively driven plates that are being read—designated with a "R", (2) plates driven as active shields—designated with a "S" (these plates are driven with a voltage that is similar to the voltage being driven on the plate that is being read), and (3) plates that are left floating—designated with an "F". Many different sensor plate 32 configurations are possible. For example, SSSSSSRSSSSSS implies that the first 6 plates are driven as active shields, the center plate is a driven and read plate, and then the final 6 plates are driven as active shields. By comparing readings between two different configurations of plates, a property of the surface material can be estimated. There are many different configurations of plates that can be tested such as FFFFFFRFFFFFF, FFFRSSRFFFF, FFFFFRSRFFFFF, FFFFF-FRSSSSSS, SSSSSSRFFFFFF, FFFFRSSRFFF, SSSRFFRSSSS, SSSSSRRFFFFFF, FFFFRFRFRFFFF, and many others. Those skilled in the art can select the configurations that are most suitable for their application. Testing the different configurations may be the most effective means of selecting the configurations that may be most effective in a particular application. In some embodiments comparing readings from the pattern FFFRFRFRFRFFF to pattern SSSRSRSRSRSSS may be effective at estimating a surface material property. In some embodiments comparing readings from the pattern SSSSSFRFSSSSS to pattern SSSSSSRSSSSSS may be effective at estimating a surface material property. In some embodiments comparing readings from the pattern FFFRFFRFFRFFF to pattern SSSRSSRSSRSSS may be effective at estimating a surface material property. In some embodiments more than one estimation procedure is used. Those skilled with mathematics can select the patterns, or combinations of patterns that are most useful for correcting for the desired surfaces.

Some embodiments do not perform surface material calibration. For example, some embodiments that are only designed to operate on one type of surface may not perform surface material calibration.

In some embodiments, after a surface material property is estimated, the readings are adjusted. In some embodiments an estimate of a property of the surface is multiplied by a correction factor(s) to create an adjustment value(s), the adjustment value(s) is then added to, or subtracted from, the measured capacitance(s) to correct the capacitance reading(s). In some embodiments a first correction factor is applied to correct a capacitance reading from a location that is near the edge of the detector, and a second correction factor is applied to correct a capacitance reading from a location that is near the center of the detector.

In some embodiments the correction factor(s) comprise a predetermined set of values that are stored in a non-volatile memory. The predetermined set of values can be scaled, where the scaling factor is the surface material property. In some embodiments the scaled set of values can then be added to, or subtracted from, the readings. Other embodiments may use calibration adjustments that comprise multiplication, or division, or other mathematical functions.

In some embodiments, after calibrating the sensor plate readings the detector 10 decides if an obscured feature is present. In some embodiments the lowest sensor plate reading is subtracted from the highest sensor plate reading. If the difference is greater than a threshold value then a determination is made that an obscured feature is present. See FIG. 8.

If it is determined that no obscured features are present, then all of the indicators 52 may be deactivated. If an obscured feature is present then the detector 10 begins the process of determining the position(s) and width(s) of the obscured feature(s).

In some embodiments, the next step is to scale the all of the current sensor plate readings such that the lowest reading is scaled to a predetermined value (such as 0) and the maximum reading is scaled to a second predetermined value (such as 100). All intermediate values may be scaled proportionately. Scaling the readings may make it easier to compare the readings to a set of predetermined patterns.

In some embodiments a pattern matching module is used to determine the location of obscured features. The pattern matching module compares the calibrated and scaled readings from the sensor plates 32 to predetermined patterns to identify the pattern that best matches sensor plate readings. The calibrated and scaled readings may also be referred to as current readings, or simply readings. A set of calibrated and scaled readings may be referred to as a measured reading pattern.

In some embodiments the pattern matching module uses a measured reading pattern as an input. In some embodiments, the measured reading pattern is comprised of the group of the current sensor plate readings that have been calibrated and scaled. The pattern matching module uses a plurality of predetermined patterns, each predetermined pattern comprising a set of predetermined values. The module compares the reading pattern to each of the predetermined patterns. Then the pattern matching module determines which predetermined pattern most closely matches the reading pattern. After the closest-matching pattern is determined, the location of one or more obscured features can be identified. In some embodiments, the set of predetermined patterns may consist of, for example, a pattern that is consistent with the detector performing a reading on surface of sheetrock 80 with a single stud 95 behind the sheetrock 80. The set of predetermined patterns may include multiple patterns corresponding to a single stud 95, where each pattern corresponds to a single stud 95 in a different location. Another predetermined pattern may be consistent with the detector performing a reading on a surface of sheetrock 80 with two studs 95 behind the sheetrock 80, the two studs 95 separated by about two inches. In some embodiments, the set of predetermined patterns may include predetermined patterns that correspond to three obscured features, so that it may be possible to detect three or more features simultaneously. In some embodiments, the set of predetermined patterns may include predetermined patterns that correspond to features with different widths, which may enable the detector to identify the width of an obscured feature. Many different patterns can be created, corresponding to different sizes of obscured features, different locations of obscured features, different numbers of obscured features, or obscured features with different material compositions. In some embodiments approximately one hundred and fifty predetermined patterns may be used. In some embodiments approximately one hundred and fifty unique predetermined patterns may be used. In some embodiments the number of predetermined patterns is at least 30 unique patterns. In some embodiments the predetermined patterns may correspond to obscured features that are studs 95. In some embodiments the predetermined patterns may correspond to other obscured features such as pipes, wires, rebar, conduit, beams, metal studs, 50 and 60 Hz electric fields, or other obscured features.

Figure 9:
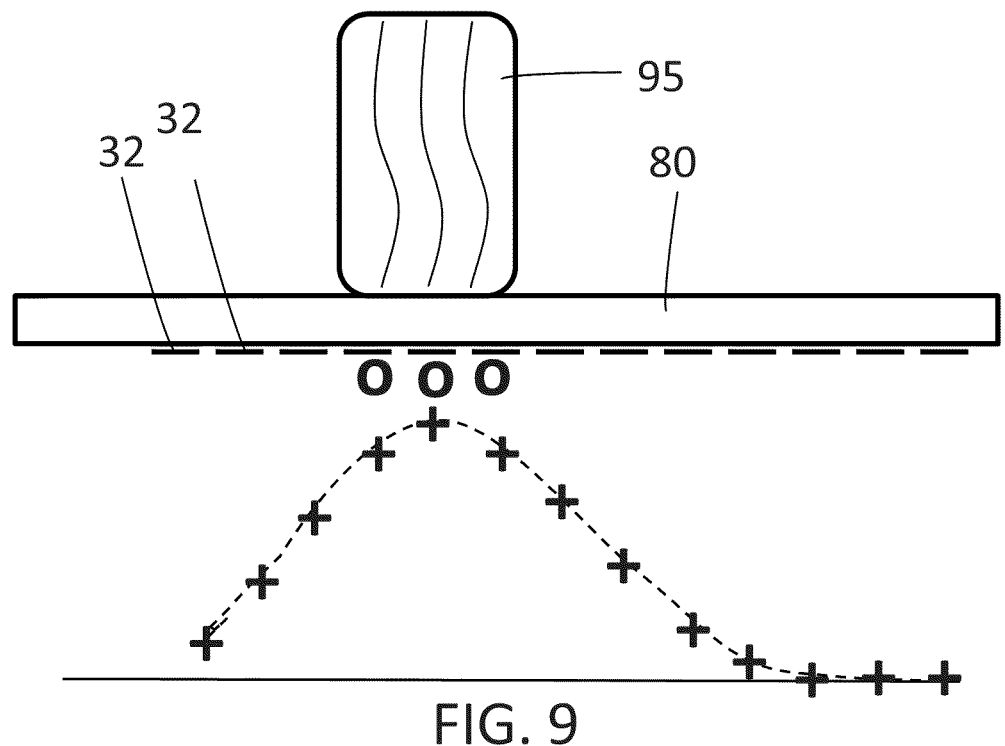
FIG. 9 is an illustration of a set of values that comprise an example of one particular predetermined pattern. The "+" symbols represent the values of a predetermined pattern; larger values are higher on the page. In this example there is a surface and thirteen sensor plates. It is an example of a predetermined pattern with a single stud. The "o" symbols represent the location of indicators that may be activated if this pattern were selected as the best matching pattern.
Figure 10:
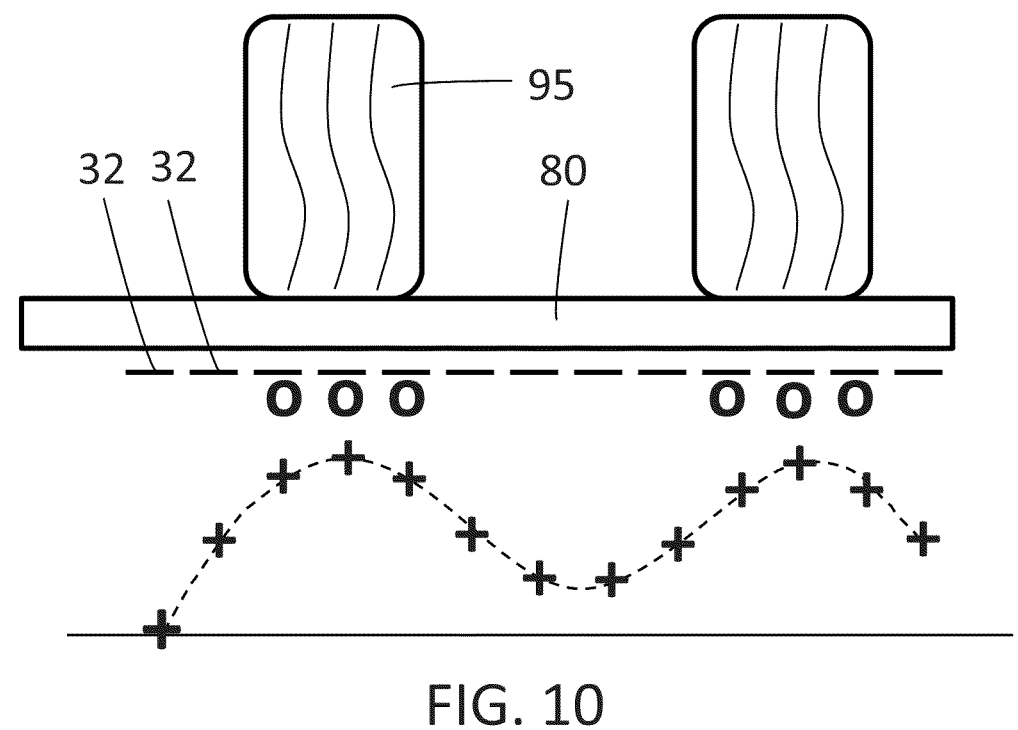
FIG. 10 is an illustration of a set of values that comprise an example of one particular predetermined pattern. The "+" symbols represent the values of a predetermined pattern; larger values are higher on the page. In this example there is a surface and thirteen sensor plates. It is an example of a predetermined pattern with two studs. The two studs are separated by a distance of about two inches. The "o" symbols represent the location of indicators that may be activated if this pattern were selected as the best matching pattern.
Figure 11:
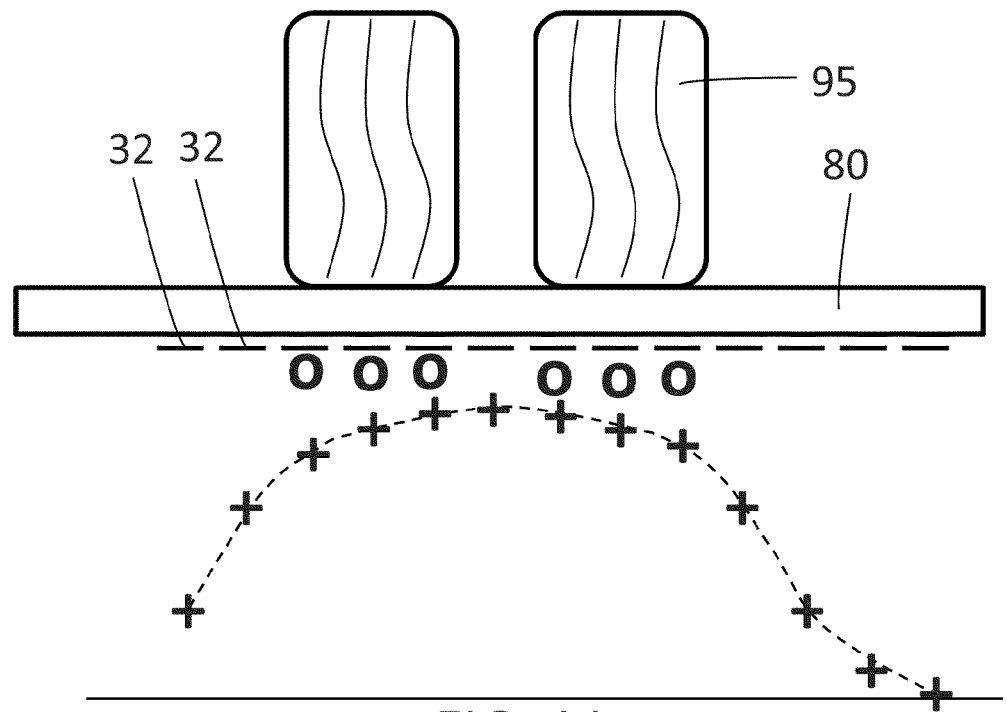
FIG. 11 is an illustration of a set of values that comprise an example of one particular predetermined pattern. The "+" symbols represent the values of a predetermined pattern; larger values are higher on the page. In this example there is a surface and thirteen sensor plates. It is an example of a predetermined pattern with two studs. The two studs are separated by a distance of about one half of an inch. The "o" symbols represent the location of indicators that may be activated if this pattern were selected as the best matching pattern.
Figure 12:
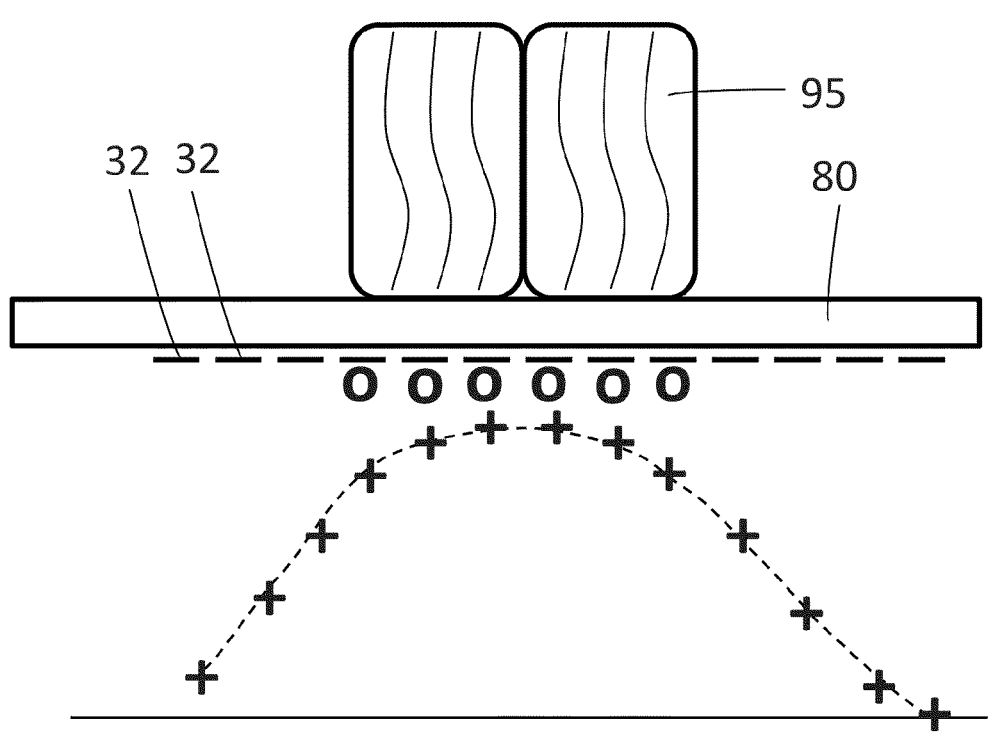
FIG. 12 is an illustration of a set of values that comprise an example of one particular predetermined pattern. The "+" symbols represent the values of a predetermined pattern; larger values are higher on the page. In this example there is a surface and thirteen sensor plates. It is an example of a predetermined pattern with two studs. The two studs next to each other. The "o" symbols represent the location of indicators that may be activated if this pattern were selected as the best matching pattern.

FIGS. 9, 10, 11, and 12 illustrate embodiments with thirteen sensor plates 32. Each of the figures shows the thirteen sensor plates 32 and a surface. The "+" symbols in each of the figures represent the values that comprise a predetermined pattern. In some embodiments, each of the predetermined patterns is comprised of thirteen values. For example in FIG. 9 there are thirteen "+" symbols which correspond to the thirteen values which comprise a predetermined pattern. In this particular example, each of the sensor plates 32 corresponds to one value in a predetermined pattern. In some embodiments there is one value in the predetermined pattern for each sensor plate 32. In some embodiments there may be more values in the predetermined pattern than there are sensor plates 32. In some embodiments there may be fewer values in the predetermined pattern than there are sensor plates 32. FIG. 9 illustrates the values of a predetermined pattern for a surface with a single stud 95 behind it. FIG. 10 illustrates the values of a predetermined pattern for a surface with two studs 95 behind it, the two studs 95 being spaced about two inches apart. FIG. 11 illustrates the values of a predetermined pattern for a surface with two studs 95 behind it, the two studs 95 being about one half inch apart. FIG. 12 illustrates the values of a predetermined pattern for a surface with two studs 95 behind it, the two studs 95 being next to each other. In each of the examples in FIGS. 9, 10, 11, and 12 the letter "o" represents the indicators 52 that may be associated with each of the patterns. The letter "o" in FIGS. 9, 10, 11, and 12 represents the indicators 52 that may be activated if each respective pattern were to be selected as the best matching predetermined pattern. FIGS. 9, 10, 11, and 12 show four representative predetermined patterns, corresponding to each of four different combinations of obscured features. Many more than four predetermined patterns may be used in some embodiments. In some embodiments there is one indicator 52 that is associated with each sensor plate 32. Other embodiments may have more, or fewer, indicators 52 than sensor plates 32.

Figure 13:
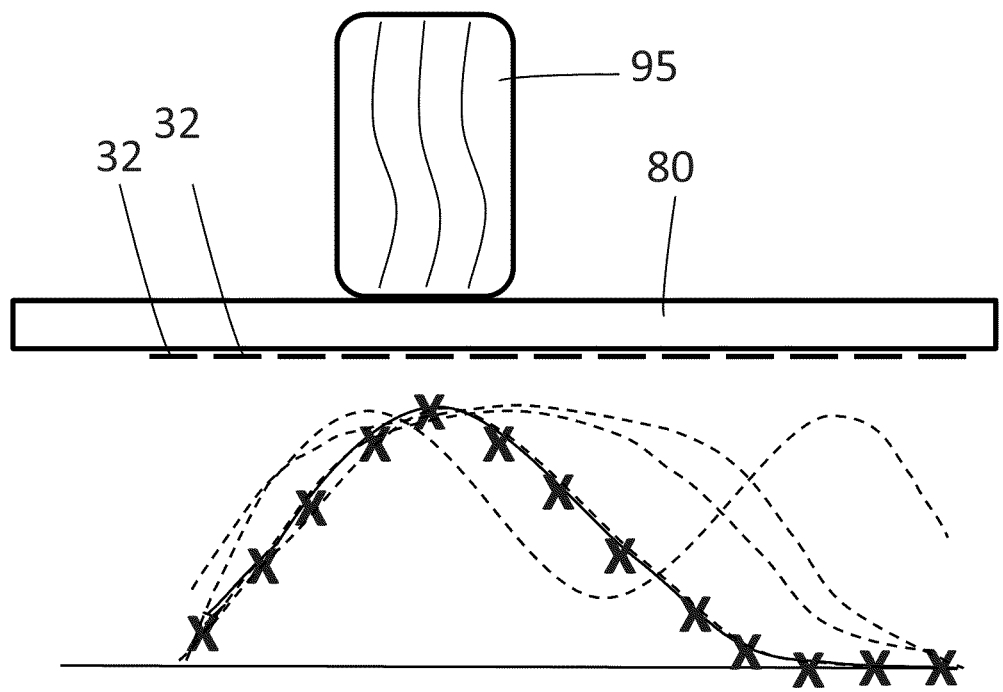
FIG. 13 is an illustration of a surface and thirteen sensor plates. The "x" symbols represent the values of the readings; larger readings are higher on the page.

FIG. 13 illustrates the measured reading patterns, as represented by the symbol "x". Superimposed on the image are representations of the four different predetermined patterns from FIGS. 9, 10, 11, and 12. The pattern matching module selects the best matching pattern, and activates the indicators 52 associated with the best matching pattern.

In some embodiments the set of predetermined patterns can be determined in advance by physically testing each configuration using an actual surface material, such as sheetrock 80, and an actual obscured feature(s), such as stud(s) 95, then storing the results of the readings as the pattern for each respective configuration.

In some embodiments a single pattern may be determined by physically testing a particular configuration with an actual surface and an actual obscured feature, and then other patterns may be derived from the tested pattern. For example a predetermined pattern could be determined by reading the sensor plates 32 through a surface, with an obscured feature, such as a stud 95 on the opposite side. Then, the other patterns could be derived from this single-feature pattern. For example, the values for other patterns that involve a single stud 95 could be created by shifting the one tested pattern to other positions.

In some embodiments dual-feature patterns are derived from two single-feature patterns. In some embodiments two single-feature patterns can be added together to create the pattern that represents a configuration with two obscured features.

In some embodiments the complete set of predetermined patterns are stored in non-volatile memory at the factory. In some embodiments the set of predetermined patterns are calculated from the single-feature pattern by the program and stored in memory each time the detector 10 is initialized. In some embodiments the predetermined patterns are calculated and stored in ROM (read-only memory) when a calibration routine in executed. In some embodiments each predetermined pattern is calculated in real-time, just before it is needed.

In some embodiments each of the predetermined patterns are scaled such that the lowest value in the pattern is zero and the highest value in the pattern is one hundred. Likewise in some embodiments the reading pattern is scaled such that the lowest value in the pattern is set to zero and the highest value in the pattern is scaled to one hundred. In some embodiments the patterns and readings are scaled such that the highest value is 255, corresponding to the maximum number that can fit in a single computer byte.

In some embodiments the reading pattern is compared to each of the predetermined patterns and a score is given to each comparison. The score represents the amount of similarity between the reading pattern and the predetermined pattern. A lower score represents more similarity between the reading pattern and the respective predetermined pattern. In some embodiments the score is determined by comparing each value of the reading pattern to each value of the respective predetermined pattern. The following formula is used by some embodiments to create a score based upon a comparison of the reading pattern values, to the predetermined pattern values.

$$\text{Score (based upon value comparisons)} = |R1-Px\_1| + |R2-Px\_2| + |R3-Px\_3| + \ldots + |R3-Px\_12|$$

The reading pattern is given by the set of values R0, R1, R2, ..., R12, for sensor plate0 thru sensor plate12 respectively, where each of the values R0, R1, R2, ..., R12 are calibrated and scaled readings where the minimum value is zero and the maximum value within the pattern is scaled to one hundred.

The predetermined pattern for Pattern0 is given by P0_0, P0_1, P0_2, ..., P0_12.

The predetermined pattern for Pattern1 is given by P1_0, P1_1, P1_2, ..., P1_12.

The predetermined pattern for Pattern151 is given by P151_0, P151_1, P151_2, ..., P151_12.

Each of the predetermined patterns consists of calibrated and scaled values where the minimum value within the pattern is zero and the maximum value within the pattern is scaled to one hundred.

In some embodiments a score is calculated by comparing the slope of various segments of the reading pattern to the slope of various segments of each predetermined pattern.

In some embodiments slope segments are based upon slopes that are created by comparing readings from plates that are one sensor plate 32 apart. In some embodiments slope segments are based upon slopes that are created by comparing readings that are adjacent, adjacent readings that are one apart. Some embodiments use the following formula.

$$\text{Score Based on Slope, Using a Slope That is Calculated by Comparing Readings From Plates that are One Sensor Plate Apart} = |(R1-R0)-(Px\_1-Px\_0)| + |(R2-R1)-(Px\_2-Px\_1)| + |(R3-R2)-(Px\_3-Px\_2)| + \ldots + |(R12-R11)-(Px\_12-Px\_11)|$$

Table 1 in FIG. 14 shows an example of the calculation of the score using this scoring method. In this example two predetermined patterns, Predetermined Pattern A and Predetermined Pattern B are compared to the Measured Reading Pattern. The absolute values of the differences between the Measured Reading Pattern values and each of the values of the Predetermined Pattern are calculated, and scores are calculated. A lower score identifies a closer match between the Measured Reading Pattern and the respective predetermined pattern.

In some embodiments slope segments are based upon slopes that are created by comparing readings from sensor plates 32 that are two sensor plates 32 apart. In some embodiments slope segments are based upon slopes that are created by comparing readings that are two apart. Some embodiments use the following formula.

$$\text{Score Based on Slope, Using a Slope That is Calculated by Comparing Readings From Plates that are Two Sensor Plate Apart} = |(R2-R0)-(Px\_2-Px\_0)| + |(R3-R1)-(Px\_3-Px\_1)| + |(R4-R2)-(Px\_4-Px\_2)| + \ldots + |(R12-R10)-(Px\_12-Px\_10)|$$

Table 2 in FIG. 15 shows an example of the calculation of the score using this scoring method. In this example two predetermined patterns, Predetermined Pattern A and Predetermined Pattern B are compared to the Measured Reading Pattern. Slopes between values of the predetermined patterns are calculated. The absolute values of the differences between the slopes are calculated. A lower score identifies a closer match between the Measured Reading Pattern and the respective predetermined pattern.

In some embodiments plates slopes segments are based upon slopes that are created by comparing readings from plates that are three sensor plates 32 apart. In some embodiments slope segments are based upon slopes that are created by comparing readings that are three apart. Some embodiments use the following formula.

$$\text{Score Based on Slope, Using a Slope That is Calculated by Comparing Readings From Plates that are Three Sensor Plate Apart} = |(R3-R0)-(Px\_3-Px\_0)| + |(R4-R1)-(Px\_4-Px\_1)| + |(R4-R2)-(Px\_4-Px\_2)| + \ldots + |(R12-R10)-(Px\_12-Px\_10)|$$

Some embodiments use a combination of multiple scoring formulas. Some embodiments use the score based upon value comparisons to help determine the best matching pattern. Some embodiments use score based on slope, using a slope that is calculated by comparing readings from plates that are one sensor plate 32 apart to help determine the best matching pattern. Some embodiments use score based on slope, using a slope that is calculated by comparing readings from plates that are two sensor plates 32 apart to help determine the best matching pattern. Some embodiments use score based on slope, using a slope that is calculated by comparing readings from plates that are three sensor plates 32 apart to help determine the best matching pattern. Some embodiments determine the score by using the sum of the results of the four different described scoring schemes: score based upon value comparisons, score based upon slope comparisons from plates that are one plate apart, score based upon slope comparisons from plates that are two plates apart, score based upon slope comparisons from plates that are three plates apart. Many different scoring methods are possible.

In some embodiments the lowest score is selected as the best-matching pattern. In some embodiments each predetermined pattern has a set of indicators 52 that are associated with it. In some embodiments the indicators 52 that are associated with the best matching pattern are activated. In some embodiments one or more of the predetermined patterns has indicator(s) 52 associated with the predetermined patterns that correspond to a set of indicators 52 that spans about one and one half inches. This may be used, for example, to indicate the location of a stud 95. In some embodiments, one more of the predetermined patterns have indicator(s) 52 associated with the predetermined patterns that correspond to the edges of an obscured feature. This may be used in some embodiments to indicate the edges of an obscured feature.

In some embodiments, different combinations of read configurations are combined. For example, in some embodiments, the second sensor plate 32 is sensed individually, followed by the first, second and third sensor plates 32 being grouped together and sensed as a unit. These two readings may then combined by the detector 10 to create a reading. Many combinations are possible.

In some embodiments, differential detection is employed, whereby one group of sensor plates 32 is compared to an alternate group of sensor plates 32. The groups of compared sensor plates 32 may, or may not, be adjacent. Each group of compared sensor plates 32 can comprise one or more sensor plates 32. Many combinations are possible. Those skilled in the art can determine which of the many combinations are most suitable for a desired design. Combining the readings from a variety of different combinations of readings, including both differential and non-differential readings, may provide composite readings that may detect more deeply, with more accuracy, and less noise.

In some embodiments the detector 10 uses a single capacitance-to-digital converter 38. In some embodiments the sensor plates 32 may be individually connected to the capacitance-to-digital converter 38. In some embodiments the sensor plates 32 may be individually connected to the capacitance-to-digital converter 38 via a multiplexer 37. In some embodiments more than one sensor plate may be connected to the capacitance-to-digital converter 38 at a time. In some embodiments multiple adjacent sensor plates 32 may be connected to the capacitance-to-digital converter. In some embodiments multiple non-adjacent sensor plates 32 may be connected to the capacitance-to-digital converter. The use of a multiplexer 37 to connect sensor plates 32 to a single capacitance-to-digital converter may improve the sensor plate to sensor plate 32 consistency of the readings, because the readings from each of the sensor plates 32 may be equally affected by variations to the capacitance-to-digital converter 38. Factors that may affect the readings from capacitance-to-digital converter 38 may include, but are not limited to process variations, temperature variations, voltage variations, electrical noise, aging, and others.

In some embodiments a detector 10 may use more than one capacitance-to-digital converter 38. In some embodiments that use more than one capacitance-to-digital converter 38 methods of calibrating the different capacitance-to-digital converters 38 to each other are employed. In some embodiments each of the individual capacitance-to-digital converters 38 are configured so that they may each read a common calibration capacitance. The calibration capacitance may be a discrete capacitor, or it may be traces on the printed circuit board 40, or another capacitance. After each capacitance-to-digital converter 38 reads the common calibration capacitance then calibration values are determined. The calibration values can be combined with the readings to bring the readings from the different capacitance-to-digital converters 38 in harmony with each other.

In some embodiments with multiple capacitance-to-digital converters 38, the capacitance-to-digital converters 38 can be calibrated to each other by having the sensor plates 32 read the capacitance of a common surface, either through the same sensor plate 32, or through different sensor plates 32. This could be accomplished, for example, by placing sensor plates 32 over a uniform surface. Differences in readings would presumably be due to differences in the capacitance-to-digital converters 38. After each capacitance-to-digital converter 38 reads the common surface then calibration values are determined. The calibration values can be combined with the readings to bring the readings from the different capacitance-to-digital converters 38 in harmony with each other.

In some embodiments, the sensor plate traces 35 are routed such that each of the sensor plate traces 35 have substantially equal capacitance, resistance, and inductance. In some embodiments it is desirable for each of the sensor plate traces 35 to have the same electrical properties, so that each of the sensor plates 32 will respond equivalently to the same detected objects.

In some embodiments each of the traces 35 from the capacitance-to-digital converter 38 to each of the sensor plates 32 has substantially the same length, as shown in FIG. 7. In some embodiments two or more of the sensor plate traces 35 from the capacitance-to-digital converter 38 to the sensor plates 32 has substantially the same length. Sensor plate traces 35 with substantially the same length may have more equivalent capacitances, inductances, and resistances. Equal length sensor plate traces 35 may offer enhanced performance because they may improve the uniformity of the readings, such that the sensor plates 32 respond more equivalently to the same detected objects, and may provide more immunity from environmental conditions, such as temperature.

In some embodiments each of the sensor plate traces 35, that comprise electrically conductive paths, have substantially the same width. In some embodiments, both the width and the length of each of the sensor plate traces 35 are made to be equivalent. In some embodiments the sensor plate traces 35 will have more than one segment. For example, a first segment of the traces may route the sensor plate traces 35 from a capacitance-to-digital converter 38 to a via. The via may take the sensor plate trace 35 to a different layer of the printed circuit board 40, where there may be a second segment of the sensor plate trace 35. In some embodiments all of the sensor plate traces 35 will have the same length and width, in each segment, as the other traces in that segment. In some embodiments two or more of the sensor plate traces 35 will have the same width throughout a first segment. In some embodiments two or more of the sensor plate traces 35 will have the same width throughout a second segment. In some embodiments two or more of the sensor plate traces 35 will have the same length throughout a first segment. In some embodiments two or more of the sensor plate traces 35 will have the same length throughout a second segment.

In some embodiments each of the traces 35 from the capacitance-to-digital converter 38 to each of the sensor plates 32 has substantially the same surroundings. In some embodiments the sensor plate traces 35 are routed sufficiently far apart so that capacitive and inductive coupling between traces 35 is minimized, and may improve consistency because each of the sensor plate traces 35 may have surroundings that are more similar to the other sensor plate traces 35. In some embodiments, as shown in FIG. 7, each of the sensor plate traces 35 are shielded on one or both sides with a shield trace 99. In some embodiments the shield trace 99 is routed at a uniform distance from the sensor plate traces 35 on both sides of each sensor plate trace 35. In some embodiments the shield traces 99 are parallel to the sensor plate traces 35.

In some embodiments, the shield traces 99 are substantially parallel to the sensor plate traces 35. In some embodiments, the shield traces 99 are positioned such that the shield traces 99 shield the sensor plate traces 35 from external electromagnetic fields. In some embodiments, two or more sensor plate traces 35 have one or more respective shield traces 99. In some embodiments, the sensor plate traces 35 and shield traces 99 are positioned such that capacitance between each sensor plate trace 35 and each respective shield trace 99 is substantially the same for each sensor plate trace 35 and its respective shield trace 99. In some embodiments a sensor plate trace 35 is accompanied by two shield traces 99, such that one shield trace is positioned on each side of the sensor plate trace. In some embodiments, a sensor plate trace 35 and a shield trace 99 are positioned such that there is a constant distance between a sensor plate trace 35 and the respective shield trace 99, along their length. In some embodiments each of the shield traces 99 are positioned at a uniform distance away from the respective sensor plate trace 35. In some embodiments a segment of the each sensor plate trace 35 and a segment of each shield trace 99 comprise copper traces on a printed circuit board 40. In some embodiments, the sensor plate traces 35 and shield traces 99 are both located on the same layer of a printed circuit board 40. In some embodiments, the shield traces 99 are driven at a fixed voltage level. In some embodiments, the shield traces 99 are driven at a voltage that is similar to the voltage driven on the first set of electrically conductive paths.

In some embodiments the shield traces 99 may be routed at a distance of approximately 0.6 mm from each sensor plate trace 35, along as much of the length of the sensor plate trace 35 as is possible. In some embodiments the sensor plate traces 35 are approximately 0.15 mm wide throughout one segment of the sensor plate trace 35.

In some embodiments the sensor plate traces 35 comprise multiple segments. In some embodiments a segment of a sensor plate trace 35 may be the wire bonds that are within the package of an integrated circuit that route the signals from the piece of silicon to the pins of the integrated circuit package. In some embodiments a segment of a sensor plate trace 35 may comprise a layer of copper on a first layer of a printed circuit board 40. In some embodiments a segment of a sensor plate trace 35 may comprise a layer of copper on a second layer of a printed circuit board 40.

In some embodiments the sensor plate traces 35 are shielded with layers of copper, such that the traces 35 are shielded both on a layer above the sensor plate traces 35, and are shielded on a layer below the sensor plate traces 35.

In some embodiments the shield traces 99 that are used for shielding may be driven at a fixed voltage value. In some embodiments the shield traces 99 may be driven with a signal that has a voltage that is similar to the signal that is driven on the sensor plates 32, or to another value. Serpentine routing may be used so that all of the sensor plate traces 35 may have the same length.

In one particular example, the obscured feature detector 10 comprises thirteen sensor plates 32 arrayed side by side in vertical orientation along the longitudinal axis of the detector 10, with a gap of approximately 1.7 mm between adjacent plates. In this particular example, each sensor plate 32 has a width of about 11 mm wide and a length of about 47 mm. In some embodiments two or more sensor plates 32 have the same length. In some embodiments two or more sensor plates 32 have the same width. In some embodiments two or more sensor plates 32 have the same thickness.

The housing 12 can be manufactured from ABS plastic. In order to accommodate the thirteen sensor plates 32, the housing 12 can have a length of about seven inches and a width of about three inches.

In some embodiments, the housing 12 has a longitudinal axis with a length of at least about 6", which advantageously enables the obscured feature detector 10 to span the full width of a common obscured feature, such as a stud 95, from a stationary position. By contrast, many existing stud detectors are not wide enough to span the full width of a stud 95 without being moved.

In other embodiments, the obscured feature detector 10 can be longer than 16", with about thirty sensor plates 32, or more. Such a configuration can be particularly advantageous, because many structures built according to standard construction methods in the United States have studs 95 spaced 16" apart on center. Thus, whenever an obscured feature detector 10 having a length greater than about 16" is placed against a wall of such a structure, the detector 10 will typically indicate the presence of at least one stud 95 on the first try.

In some embodiments the width of obscured features are identified. Some embodiments have sensor plates 32 that are spread over a distance that is wider than the detected obscured features. In some embodiments the detector activates all of the indicators 52 that are in front of an obscured feature, the activated indicators 52 indicate the position and width of the obscured features. In some embodiments an activated indicator indicates that there is an obscured feature behind the activated indicator. In some embodiments, the width of the set of activated indicators 52 indicates the width of the obscured feature. In some embodiments, the width of a continuous set of activated indicators 52 indicates the width of the obscured feature.

For example, to indicate that a three inch wide beam has been detected all the indicators 52 that are in front of the beam are activated, such that a continuous set of indicators 52 are activated over a 3 inch span, directly in front of the beam. Likewise, to indicate that a one and a half inch wide stud 95 has been detected the indicators 52 that are in front of the stud 95 are activated, such that a continuous set of indicators 52 are activated over a one and a half inch span directly in front of the beam. Some embodiments have indicators 52 that are spaced one half inch apart and identify the width of obscured features with a granularity of one half inches. Some embodiments identify the width of obscured features with a granularity of one half inches. Some embodiments have a minimum feature size of one and half inches and a granularity of one half inch, for features that are wider than one and one half inch. Many other combinations of minimum features size and granularity are possible. In some embodiments the width of multiple obscured features can be identified by multiple sets of activated indicators 52.

Advantageously, the present disclosure provides various embodiments of a surface-conforming obscured feature detector 10. Conventional detectors have sensor plates 32 that are rigidly connected together, and as a result the size of obscured feature detectors typically remains relatively small to function on the curved surfaces that are typical of many architectural surfaces. The surface-conforming feature detector 10 disclosed herein conforms to the contour of the surface, minimizes air gaps, and makes it possible to build larger feature detectors that can offer a variety of performance improvements. The improvements described in the present disclosure are applicable to both conventional detectors that are relatively small, and to larger feature detectors.

Viewing FIGS. 2 and 3, in some embodiments, the obscured feature detector 10 has one or more flexible printed circuit boards 40 that can bend to match the contour of the surface to be detected. The flexible printed circuit boards 40 comprise a flexible substrate. Other flexible substrates can also be used that can be made of wood, paper, plastic, or other flexible materials. Rigid flex printed circuit boards 40 can also be used.

The one or more printed circuit boards 40 can be flexibly connected to the housing 12 using a flexible medium such as foam rubber, springs, gel, hinges, pivot points, an encapsulated gas such as air, or other suitable compressible or flexible media. In some embodiments the housing 12 is able to flex. In some embodiments the housing 12 is partially flexible. In some embodiments the housing 12 has integrated plastic leaf springs, or other types of springs or features that provide flexibility. In some embodiments of the obscured feature detector 10, the sensor plates 32 can be mounted on a printed circuit board 40 that is mounted external to the housing 12, as seen in FIGS. 2 and 3. In some embodiments the printed circuit board 40 is connected to the housing 12 via a foam rubber ring 70. In some embodiments, the foam rubber ring 70 is about seven millimeters thick and is formed approximately in the shape of a ring that is about six millimeters wide along the long side, and about five millimeters thick along the short side, and approximately follows the perimeter of the housing 12. A permanent adhesive, such as a pressure sensitive acrylic adhesive, can be used to bond the foam rubber ring 70 to the housing 12 and to the printed circuit board 40.

In some embodiments, the foam rubber ring 70 is compressible, and the printed circuit board 40 is flexible, allowing the obscured feature detector 10 to conform to curvature and irregularities of a surface against which it is placed. A variety of flexible and/or compressible materials can be suitable for the flexible medium. EPDM foam rubber that is rated for 25% compression under about 1.5 pounds per square inch of pressure can be used. Other types of foam rubber such as polyurethane foam or silicon rubber foam can also be used. In some embodiments it is desirable that the flexible medium attached between the printed circuit board substrate and the housing 12 not be electrically conductive or partially conductive, at least not to the extent that it would interfere with to operation of the detector 10.

FR-4 and Rogers 4003, and other printed circuit board substrates have sufficient flexibility to bend to match the contour of many architectural surfaces. In some embodiments that use FR-4, a variety of FR-4 with a high dielectric breakdown can be used to protect from electrostatic discharge. S1141 from Guangdong Shengyi has a dielectric breakdown of greater than 40 kV/mm which provides good electro-static discharge protection, compared to some versions of FR-4, which may have a typical dielectric breakdown of about 20 kV/mm. Many varieties of FR-4 may be suitable.

In some embodiments a 1.6 mm thick printed circuit board 40 with four layers of copper can be used. As illustrated in FIG. 19 the first layer of copper is on the upper surface and all of the electrical components are soldered to this layer. The second layer of copper can be at a position that is about 0.35 mm below the first layer of copper, such that there is about 0.35 mm of printed circuit board substrate between the first and second layers of copper. The third layer of copper can be at a position that is about 0.1 mm below the second layer of copper, such that there is about 0.1 mm of printed circuit board substrate between the second and third layers of copper. A fourth layer of copper can be at a position that is about 0.35 mm below the third layer of copper, such that there is about 0.1 mm of printed circuit board substrate between the third and fourth layers of copper. In some embodiments all the vias can be drilled to connect the four layers of copper.

In some embodiments a final layer of substrate material that is 0.8 mm thick can be placed to cover the fourth layer of copper. In some embodiments, no holes are drilled through the 0.8 mm thick layer of substrate. The 0.8 mm thick layer of substrate may help protect the circuit from electrostatic discharge. Alternatively, a layer of plastic, or other non-conductive material, can be used to shield the circuit from electrostatic discharge and to physically protect the printed circuit board 40. In some embodiments, a layer of plastic can be used in addition to a protective layer of circuit board substrate. It is to be understood that the v layers and thicknesses indicated here are only exemplary of one embodiment. Other combinations of layers and thicknesses, and materials, can also be used.

In some embodiments the sensor plates 32 can be placed on the fourth layer of copper. A shield to electrically protect the sensor plates 32 from electrical interference from ambient conditions, including the user's hand may be used. In some embodiments the shield may be placed on the first layer of copper. In some embodiments a solid shield the covers substantially all of the shield's area, instead of using a mesh, or stripes, or another pattern that may provide less than substantially all of the shield's area.

In some embodiments the electrically conductive paths that link the sensor plates 32 to the capacitance-to-digital converter 38 comprise sensor plate traces 35. In some embodiments the sensor plate traces 35 are placed primarily on the second layer of copper, and shields for the 35 are placed on the first and fourth layers of copper.

In some embodiments each sensor plate 32 may be on its own independent printed circuit board 40. In some embodiments each sensor plate 32 can be individually attached to the housing 12 through a flexible medium such as a spring, or foam rubber. In some embodiments the sensor plates 32 are on plastic, wood, or other appropriate materials.

In some embodiments, the obscured feature detector 10 uses a plurality of printed circuit boards 40 that can each be independently, flexibly connected to the detector housing 12.

The sensor plates 32 can be mounted on two independent printed circuit boards 40, such that approximately half of the sensor plates 32 are on a first printed circuit board 40, and approximately half of the sensor plates 32 are on a second printed circuit board 40. In this way, it may be possible to achieve a design that offers increase surface conforming capability. In some embodiments more than two independent circuit boards 40 are used.

In some embodiments, the housing 12 has flexible features that allow the housing 12 to flex or bend to adapt to the contour of a non-flat detecting surface. In one particular example, an obscured feature detector 10 uses two printed circuit boards 40. Each printed circuit board 40 is attached to the housing 12. In this particular example, the housing 12 is able to flex in the center, such that each sensor plate 32 more closely matches the contour of the surface to be detected. In some embodiments, the housing 12 is mostly or entirely flexible.

In some embodiments the integrated circuits that are soldered to the printed circuit board 40 are covered with a layer of epoxy, or a glob of epoxy, or another conformal coating which may improve the reliability of solder joints. In some embodiments the integrated circuits on the printed circuit board 40 are wire bonded to the printed circuit board 40 with chip on board technology. The chip on board technology normally involves the steps of (1) attaching bare die to the printed circuit board 40, (2) wire bonding (electrically connecting signals on the bare die to the printed circuit board 40), and (3) covering the bare die and wire bonds with a coating of epoxy, or other appropriate material. The chip on board technology may improve the reliability of solder joints. In some embodiments, some of the integrated circuits that have solder reliability issues are placed on a printed circuit board 40 that is separate from the printed circuit that contains the sensor plates 32. In some embodiments all of the integrated circuits and other electronic components are placed on a printed circuit board 40 that is separate from the printed circuit board 40 that contains the sensor plates 32.

In some embodiments a ribbon cable is soldered to the printed circuit board 40 with the sensor plates 32 to connect it to a printed circuit board 40 with the integrated circuits. A soldered-down ribbon cable, such as the flat flexible cable from Parlex, may provide a reliable connection to connect printed circuit boards 40 that experience flexing and bending. In some embodiments integrated circuits that have packages with external leads are used such as QFP packages, TSOP packages, SOIC packages, QSOP packages, or others. Components that have external leads may provide improved the solder joint reliability, as compared to packages without external leads, such as QFN packages, or BGA packages. In some embodiments leadless packages, such as QFN packages and BGA packages, are used and the connection between the packages and the PCB is reinforced using an epoxy covering, commonly referred to as a glob-top.

In some embodiments, the obscured feature detector 10 can be operated in a first mode suitable for detecting obscured features through a thin surface that may correspond to a thin piece of sheet rock, or a second mode suitable for detecting obscured features through thick surface that may correspond to a thick piece of sheetrock 80.

In some embodiments there may be one set of patterns that may be optimized for a first surface thickness, and another set of patterns that may be optimized for a second surface thickness. Embodiments that are able to select the thickness of the surface material may have optimized detection capabilities, over embodiments with patterns that are not optimized for a particular surface material.

In some embodiments, the sensor plates 32 that are near the middle of the detector 10 may respond differently than sensor plates 32 that are near the edges of the detector 10. The response of the sensor plates may vary depending upon the thickness of the surface.

Some embodiments that have more than one mode for selecting the thickness are better able to calibrate the readings, and provide more accurate readings. Embodiments that have more than one surface thickness selection mode may be able to detect features more deeply. Embodiments that have more than one surface thickness detection mode may be able to detect the position of features more accurately.

In some embodiments, the obscured feature detector 10 can operate in a first mode that may be more suitable for detecting through a first surface type, or in a second mode that may be more suitable for detecting through a second surface type. In some embodiments the first surface type may be a surface with a low dielectric constant, such as sheetrock 80. In some embodiments the second surface type may be a surface with a higher dielectric constant such as wood.

In some embodiments there may be one set of predetermined patterns that may be optimized for the first surface type, and another set of patterns that may be optimized for the second surface type. Embodiments that are able to select the nature of the surface material may have optimized detection capabilities, over embodiments with patterns that are not optimized for a particular surface material.

In some embodiments, the sensor plates 32 that are near the middle of the detector 10 may respond differently than sensor plates 32 that are near the edges of the detector 10. The response of the sensor plates 32 near the edges of the detector 10, compared to the response of sensor plates 32 near the middle of detector 10, may vary depending upon the surface material. In some embodiments the calibration procedure may be optimized for the surface type. Embodiments that have more than one mode for selecting the surface type may be able to better calibrate the readings, and provide more accurate readings. Embodiments that have more than one mode for selecting the surface type may be able to detect features more deeply. Embodiments that have more than one mode for selecting the surface type may be able to detect the position of features more accurately.

In some embodiments the mode is selected via an actuator. In some embodiments the mode is set by the controller 60. In some embodiments the mode is set by the controller 60 automatically. In some embodiments the mode is set by the controller 60 automatically after the capacitances have been read.

In some embodiments, the obscured feature detector 10 can be operated in a first mode suitable for detecting an obscured feature that is embedded within a material, such as detecting a pipe within concrete, or a second mode suitable for detecting when the obscured feature is located on the other side of a surface, such as detecting a stud 95 on the other side of a piece of sheetrock 80.

In some embodiments the detector 10 may decide whether an obscured feature is present by analyzing the disparity in the measured capacitance readings. In some embodiments, a disparity value that reflects that amount of disparity in the measured capacitance readings is determined.

In some embodiments the measured capacitance readings are compared, and if the disparity value exceeds a feature-detection threshold then the detector 10 may determine that at least one obscured feature is present. In some embodiments the detector 10 may determine that an obscured feature is present if the disparity value, determined by comparing two or more measured capacitance readings exceeds a feature-detection threshold. In some embodiments the detector 10 determines that an obscured feature is present if the difference between the largest measured capacitance readings and the smallest measured capacitance reading exceeds a feature-detection threshold.

In some embodiments, the obscured feature detector 10 has a first mode that has a higher feature-detection threshold, and a second mode with a lower feature-detection threshold. In the first mode the detector 10 may require a clearer signal before the detector 10 indicates the location of an obscured feature. The second mode, with a lower feature-detection threshold may indicate the location of more subtle features that may not be detected in the first mode. The low threshold mode may make it possible to detect features that are deeper. However the second mode, with a lower feature-detection threshold, may be more inclined to falsely indicate a feature that may not be present.

In some embodiments the mode is selected via an actuator. In some embodiments the mode is set by the controller 60. In some embodiments the mode is set by the controller 60 automatically. In some embodiments the mode is set by the controller 60 automatically after the capacitances have been read.

In some embodiments, the obscured feature detector 10 can operate in a first mode that may be more suitable for detecting obscured features that comprise a first material, or in a second mode that may be more suitable for detecting obscured features that comprise a second material.

In some embodiments, the obscured feature detector 10 can operate in a first mode that may be more suitable for detecting wooden obscured features, such as wood beams or wood studs 95, or in a second mode that may be more suitable for detecting metallic features, such as a metal studs 95 or metal beam.

In some embodiments there is a set of predetermined patterns that have values that are consistent with the detector 10 sensing wooden obscured features. In some embodiments there is a set of predetermined patterns that have values that are consistent with the detector 10 sensing metallic obscured features. In some embodiments there is a set of predetermined patterns that have values that are consistent with the detector 10 sensing plastic obscured features.

Embodiments that are able to select the nature of the detected obscured features may have optimized detection capabilities, over embodiments that are not optimized for a particular obscured feature material.

In some embodiments, the first mode, or second mode, can be selected via an actuator. In some embodiments the controller 60 sets the mode. In some embodiments the controller 60 automatically selects the mode. In some embodiments, the controller 60 automatically selects the mode after the capacitances have been measured at least once.

In some embodiments the obscured feature detector 10 has a deep sensing mode that may provide deeper sensing, and a second high accuracy mode that may provide more accurate resolution of feature positions. In some embodiments the deep sensing mode may be implemented by electrically connecting sensor plates 32 in groups of two, three or more in a rolling sweep, thereby effectively increasing the sensor plate 32 size. In single-plate mode only one sensor plate 32 may be activated at a time, which may provide more accurate determination of feature positions.

In some embodiments the obscured feature detector 10 has a normal operating mode that is suitable for detecting one or a plurality of features, and an alternate, single feature detection mode that only indicates the position of a single obscured feature.

Some embodiments of the single feature detection mode will activate indicator(s) that correspond to the single highest sensor plate reading, the highest plate being selected after all readings have been calibrated. Some embodiments of the single-object detection mode may use a pattern matching module that only searches for single obscured features.

In some embodiments, a module that only indicates the location of a single feature may be able to operate at a lower detection threshold, which may make it possible to find features that would be below the noise threshold in the normal operating mode. A module that only indicates the location of a single feature may provide more consistent readings on some materials. A module that only indicates the location of a single feature may provide the user with better readings on some materials.

In some embodiments, the obscured feature detector 10 has a fast detection mode that may provide quicker detection and may provide quicker updates to the indicators 52, but may provide less accuracy and may provide less deep detection, and a slow detection mode that may provide slower detection but may be able to sense more deeply or more accurately.

In some embodiments the fast detection mode uses fewer readings to create the sensor plate readings. For example in some embodiments the fast detection mode creates a reading by summing twelve readings of the sensor plates 32.

In some embodiments the slow detection mode uses more readings to form the sensor plate readings. For example in some embodiments the slow detection mode creates a reading by summing twenty-four readings of the sensor plates 32.

In some embodiments the obscured feature detector 10 has a mode for detecting live wires, such as 50 Hz and 60 Hz wires that may carry 115V, 230V, or other voltages.

In some embodiments the capacitance-to-digital converter 38 reads each of the sensor plates 32 at least approximately six times per cycles. This implies that it reads the sensor plates 32 at least approximately 360 times per second, to detect 60 Hz. Reading the sensors plates at least six times per second may provide readings that approximately reflect all of the phases of the cycle. In some embodiments the sensor plates 32 are read more than six times per cycle, which may provide improved performance. In some embodiments regions with more disparity in the readings are identified as regions that are closer to an alternating electromagnetic field.

In some embodiments the sensing circuit performs capacitive readings at a frequency that is an inharmonic of the detected electromagnetic field frequency, and may provide readings that approximately reflect all of the phases of the cycle. In some embodiments the sensing circuit performs capacitive readings at a higher frequency than the detected electromagnetic field frequency. In some embodiments the sensing circuit performs capacitive reads at least approximately 150 times per second.

In some embodiments the detector 10 compares the readings from the different segments of the cycle. The sensor plate 32 readings that have the most disparity may be nearest to live wires. In some embodiments the detector 10 compares multiple capacitive readings from a single region to determine the amount of disparity in the readings for each respective region. For example multiple readings from a first region may be compared to each other readings from the first region to create a value that reflects the amount of disparity in the readings in the first region. Likewise, multiple readings from a second region may be compared to each other to create a value that reflects the amount of disparity of the readings in the second region. Similar readings may be made for each region, and a value that reflects the amount of disparity may be determined for each respective region.

To decide which indicators 52 to activate, in some embodiments, the same modules that are used to determine the location of obscured features can be adjusted by those skilled in the art to determine the location of live wires.

In some embodiments values that represent the disparity in the capacitance readings comprise a disparity reading pattern; a pattern matching module is configured to compare the disparity reading pattern, with a plurality of predetermined electromagnetic field patterns to determine which predetermined electromagnetic field pattern best matches the disparity reading pattern. In some embodiments a set of indicators 52 are associated with each predetermined electromagnetic field pattern. In some embodiments the indicators 52 that are associated with the best-matching electromagnetic field pattern are activated. Those skilled in the art can modify the pattern matching module that detects obscured features, so that it identifies the location of electromagnetic fields that are associated with live wires.

In some embodiments the region that has the highest disparity reading is identified as the region that is closest to an electromagnetic field that is associated with live wires, if the reading exceeds a threshold value.

In some embodiments of the detector 10 the indicators 52 that are used to detect the position of an obscured features are the same indicators 52 that are used indicate the location of electromagnetic fields. In another embodiment one set of indicators 52 is used to indicate the location of electromagnetic fields, and a second set of indicators 52 is used to indicate the position of obscured features.

In some embodiments the live wire detection runs simultaneous with obscured feature detection. In some embodiments the detector 10 provides an alert to warn that live wires are being detected. In some embodiments indicators 52 may flash to indicate that live wires are being detected. In some embodiments indicators 52 may change to a different state to indicate that live wires are being detected. In some embodiments the indicators 52 may comprise LEDs (Light Emitting Diodes) that may change to an alternate color to indicate the proximity to a live wire. In some embodiments the obscured feature detector 10 has a first mode that is suitable for detecting the location obscured features, and a second mode that is suitable for detecting the presence of the electromagnetic fields that are associated with live wires. In some embodiments the detector 10 is optimized to detect electromagnetic fields with a frequency of approximately 50 to 60 Hz.

Figure 18:
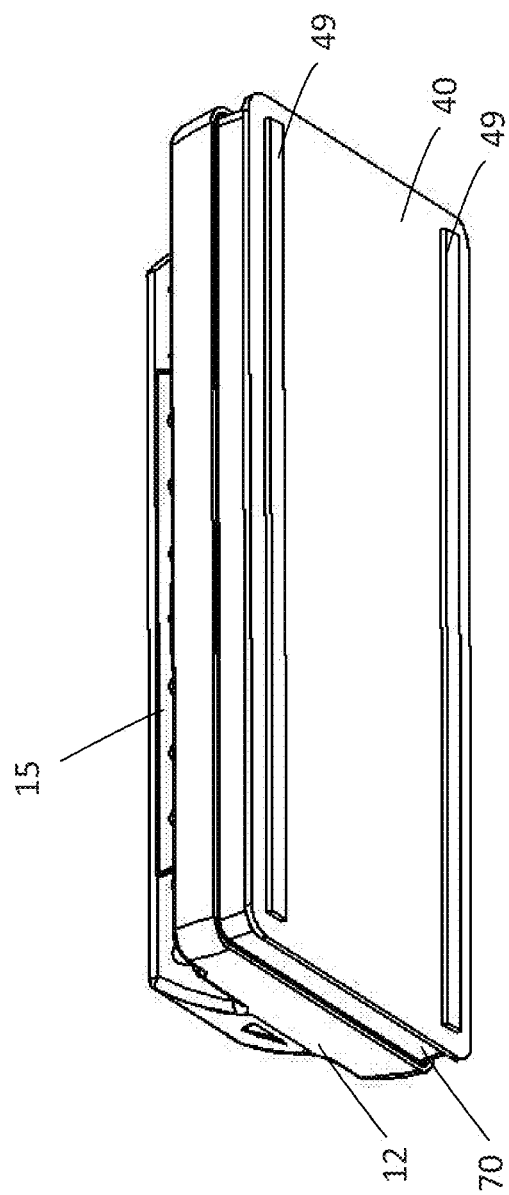
FIG. 18 is a perspective view of yet another embodiment of an obscured feature detector.

In some embodiments, as shown in FIG. 18, a layer of protective material 49 is mounted to the bottom of the detector 10, such that there is a layer of protective material 49 between the wall and the detector 10. The protective material 49 that has the interior substantially filled up such that it is substantially free from cavities, such as plastic. The protective material 49 is unlike felt, velcro, cloth, or other materials that have an interior with cavities. The layer of protective material 49 may serve the purpose of protecting the bottom of the detector 10 from damage due to knocks, bumps, and wear-and-tear. The protective material 49 could be made from a solid piece of material, such as plastic or other solid non-conductive materials. A solid layer of plastic may provide a low friction surface that would allow the detector 10 to slide across the wall. Although some embodiments of the detector 10 do not require sliding or operate, low friction may be useful to some users that may choose to move the detector 10 from position-to-position by sliding it.

The protective layer of plastic may be mounted with a pressure sensitive adhesive, glue, or other means. The layer of protective material 49 may be a complete layer that covers the entire surface; it may be rectangular strips, round pieces, or other layers of plastic with other geometries.

A protective material 49 that is substantially filled up such that it is substantially free from cavities may build up less static charge than prior art solutions and may advantageously provide for more consistent readings.

In some embodiments the protective material 49 is UHMW-PE (Ultra-High Molecular Weight Polyethylene). UHMW-PE has a low coefficient of friction. UHMW-PE also absorbs very little moisture which may provide increased immunity from changes in humidity, and may provide enhanced immunity from changes in humidity.

In some embodiments the obscured feature detector 10 can make a mark on the detected surface to indicate the location of obscured features. Some embodiments use a marker, such as a pencil-type marker to mark the location of obscured features. Some embodiments provide for multiple markers, that may be positioned a various positions along the length of the detector 10, whereby a marker may be located at each position where a mark may need to be made. Of the plurality of markers, only the markers that are in a location where a mark is desired are activated.

Some embodiments of the obscured feature detector 10 provide a single marker that can be moved to the position of an obscured feature. In some embodiments the marker uses graphite, similar to the graphite found in a pencil. Graphite-type marking methods are robust, well-proven, don't dry up, and can easily be erased from the surface. In other embodiments other types of marking materials are used.

Some embodiments may indicate the presence of features that may be so large that substantially all of the sensor plates 32 may be over a feature. Features that are this large may be called large features 96, or large obscured features 96. If the detector 10 is initially placed over a large feature 96, such that substantially all of the sensor plates 32 are over the large feature 96, all of the readings from the sensor plates 32 may have substantially the same value. This may cause the detector 10 to indicate that there are not any obscured features present. However, some embodiments provide a module that allows the obscured feature detector 10 to indicate the presence of features that are so large that substantially of the sensor plates 32 may be over the feature.

In some embodiments, when it is determined that there is an obscured feature in a particular region, a memory will record the value of the capacitance reading that existed at the time that the obscured feature was present. Then, subsequently if it is determined that a new capacitance reading has a value that is near the value stored in memory, then the indicators 52 associated with the respective region(s) may be activated. The procedure may allow the detector 10 to activate indicators 52 even when at least most of sensor plates 32 are over a feature.

In some embodiments, the detector 10 may indicate that it is over a large obscured feature 96 if the detector 10 first determines that the detector 10 is over region where a large feature 96 may be present, then if subsequently all of the sensor plate readings are substantially similar. FIG. 16 illustrates an obscured feature detector 10 that is partially over a large feature 96; the detector 10 has some of the indicators 52 activated. The detector 10 may be approaching a region where a large feature 96 may be present.

In some embodiments, the detector 10 may decide that a very large obscured feature 96 is present if an increasing number of indicators 52 become activated, increasing in number from one side of the detector 10 to the other. In some embodiments, the detector 10 may indicate that it is over a large obscured feature 96, if it was previously over region where a large feature 96 may be present approaching a large feature 96, then subsequently all of the sensor plate readings are substantially similar, and if the sensor plate readings are above a threshold value.

In some embodiments the detector 10 may indicate that it is over a large obscured feature 96 if in a first time period many of the indicators 52 are activated and if in a second time period all of the sensor plate readings are substantially similar. In some embodiments the detector 10 may indicate that it is over a large obscured feature 96 if all of the sensor plate readings are substantially similar and if the sensor plate readings are above a threshold value. In some embodiments the detector 10 may indicate that it is over a large obscured feature 96 if in a first time period the detector 10 had an indication that it was over region where a large feature 96 may be present and if in a second time period all of the sensor plate readings are substantially similar.

Figure 17:
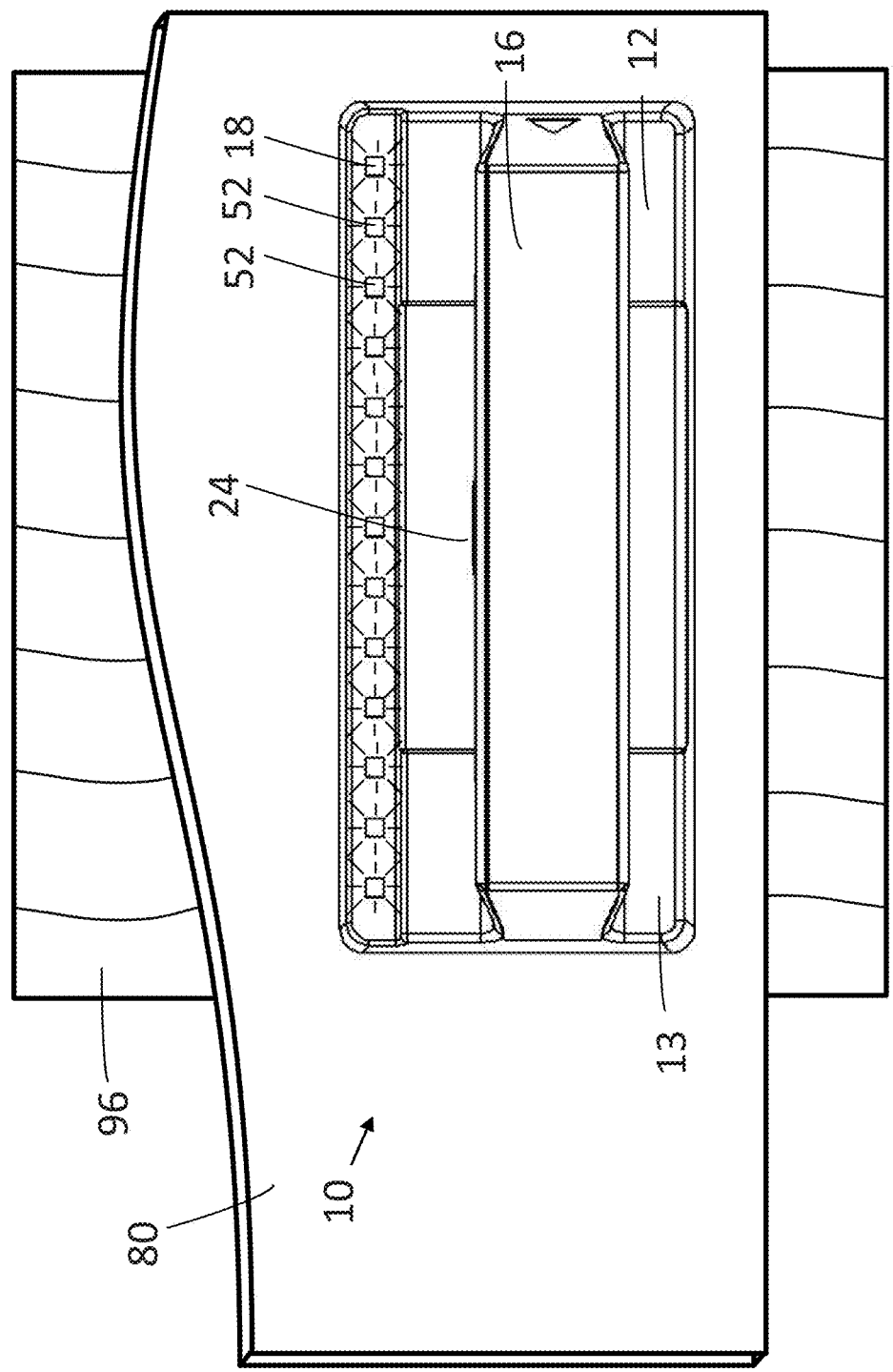
FIG. 17 is a perspective view of another embodiment of an obscured feature detector configured to detect large obscured features.

In some embodiments the detector 10 may indicate that it is over a large obscured feature 96 if in a first time period the detector 10 sensed capacitive readings that are consistent with the detector 10 being near a large obscured feature 96 and if in a second time period all of the sensor plate readings are substantially similar. In some embodiments the detector 10 may indicate that it is over a large obscured feature 96 if in a first time period the detector 10 sensed capacitive readings that are consistent with the detector 10 being near a large obscured feature 96 and if in a second time period all of the sensor plate readings are substantially similar. In some embodiments the detector 10 may indicate that it is over a large obscured feature 96 if in a first time period the detector 10 sensed capacitive readings that are consistent with the detector 10 being near a large obscured feature 96 and if in a second time period one or more of the sensor plates 32 are above a threshold value. In some embodiments, the detector 10 may activate all of the indicators 52 to indicate that the detector 10 is over a large obscured feature 96. FIG. 17 illustrates an obscured feature detector 10 that is over a large feature 96; the detector 10 has all of the indicators 52 activated.

What is claimed is:

1. An obscured feature detector comprising:
   a plurality of sensor plates, each having a capacitance that varies based on: (a) the proximity of the sensor plate to one or more surrounding objects, and (b) the dielectric constant(s) of the surrounding object(s);
   a sensing circuit coupled to the sensor plates, the circuit being configured to measure the capacitances of the sensor plates;
   a controller coupled to the sensing circuit, the controller including a processor and memory storing an algorithm configured to analyze the capacitances measured by the sensing circuit; and
   one or more indicators coupled to the controller, each indicator capable of toggling between a first state and a second state,
   wherein, when the controller detects two or more separated obscured features, the controller is configured to toggle two or more indicators from the first state to the second state simultaneously to identify the locations of the two or more separated obscured features, with one or more indicators in the first state located between the two or more toggled indicators in the second state, wherein the number of indicators in the first state identifies the width of a gap between the separated obscured features.

2. The obscured feature detector of claim 1 wherein the detector is at least approximately seven inches wide.

3. The obscured feature detector of claim 1 wherein the number of sensor plates is 4 or greater.

4. The obscured feature detector of claim 1 wherein each of the sensor plates are substantially the same size.

5. The obscured feature detector of claim 1 wherein the detector is capable of detecting three or more features simultaneously.

6. The obscured feature detector of claim 1 wherein the detector is capable identifying the width of more than one feature.

7. The obscured feature detector of claim 1, further comprising a pattern matching module configured to compare the measured capacitance readings with a plurality of predetermined patterns and determine which predetermined pattern best matches the measured capacitance readings.

8. A method for determining the location of a plurality of separated obscured features behind a surface, the method comprising:

placing an obscured feature detector on the surface, the obscured feature detector having a plurality of sensor plates arranged in an array;

measuring capacitance readings sensed in a plurality of regions, each region corresponding to an area surrounding one or more of the sensor plates;

analyzing the capacitance readings with a controller including a processor and memory storing an algorithm configured to analyze the capacitance readings;

identifying, based upon the measured capacitance readings, the location of the plurality of separated obscured features; and toggling two or more indicators from a first state to a second state simultaneously to identify the locations of the plurality of separated obscured features, with one or more indicators in the first state located between the two or more toggled indicators in the second state, wherein the number of indicators in the first state identifies the width of a gap between the separated obscured features.

9. The method of claim 8, wherein identifying the location of the plurality of obscured features comprises using a pattern matching module to determine the locations of the plurality of obscured features.

* * * * *